United States Patent
Nakamura et al.

(10) Patent No.: US 10,660,504 B2
(45) Date of Patent: May 26, 2020

(54) FLEXIBLE TUBE INSERTION APPARATUS

(71) Applicant: OLYMPUS CORPORATION, Tokyo (JP)

(72) Inventors: Shuji Nakamura, Akishima (JP); Takeshi Takahashi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 166 days.

(21) Appl. No.: 16/016,800

(22) Filed: Jun. 25, 2018

(65) Prior Publication Data
US 2018/0303313 A1    Oct. 25, 2018

Related U.S. Application Data

(63) Continuation of application No. PCT/JP2015/086397, filed on Dec. 25, 2015.

(51) Int. Cl.
*A61B 1/00* (2006.01)
*A61B 1/005* (2006.01)
(Continued)

(52) U.S. Cl.
CPC .......... *A61B 1/00006* (2013.01); *A61B 1/00* (2013.01); *A61B 1/0055* (2013.01);
(Continued)

(58) Field of Classification Search
CPC .......... A61B 1/00004; A61B 1/00064; A61B 1/00071; A61B 1/005; A61B 1/0051;
(Continued)

(56) References Cited

U.S. PATENT DOCUMENTS

| | | | | |
|---|---|---|---|---|
| 5,482,029 A | * | 1/1996 | Sekiguchi | A61B 1/00039 600/109 |
| 2007/0149852 A1 | * | 6/2007 | Noguchi | A61B 1/00082 600/144 |
| 2010/0191056 A1 | * | 7/2010 | Tanaka | A61B 1/005 600/117 |

FOREIGN PATENT DOCUMENTS

| | | |
|---|---|---|
| JP | S61-37931 A | 2/1986 |
| JP | H06-70879 A | 3/1994 |
| WO | WO 2006/028019 A1 | 3/2006 |

OTHER PUBLICATIONS

International Search Report dated Mar. 29, 2016 issued in PCT/JP2015/086397.
(Continued)

*Primary Examiner* — Jason E Flick
(74) *Attorney, Agent, or Firm* — Scully, Scott, Murphy & Presser, P.C.

(57) ABSTRACT

In a flexible tube insertion apparatus, at least one circuit determines whether an S-shape is formed in an insertion section based on a shape information of the insertion section detected by a detector, determines whether an intersection angle between an extension line of a central axis of the insertion section and a tangential line for the insertion section at an inflection point is enlarged or not based on the shape information, and determines whether or not the stiffness variable portions are provided in a position of the S-shape in the insertion section when it is determined that the S-shape is formed and the intersection angle is enlarged. A stiffness controller increases a stiffness of the stiffness variable portions included in the position of the S-shape in accordance with the determination of the circuit.

13 Claims, 14 Drawing Sheets

(51) Int. Cl.
*A61M 25/00* (2006.01)
*A61M 25/01* (2006.01)

(52) U.S. Cl.
CPC ..... *A61B 1/00078* (2013.01); *A61M 25/0102* (2013.01); *A61M 2025/0058* (2013.01); *A61M 2025/0063* (2013.01)

(58) Field of Classification Search
CPC ... A61B 1/00; A61B 1/00006; A61B 1/00078; A61B 1/0055; A61M 2025/0058; A61M 2025/0063; A61M 25/0102; A61M 25/00; A61M 25/0043; A61M 25/01
USPC ...................................................... 604/95.01
See application file for complete search history.

(56) References Cited

OTHER PUBLICATIONS

English translation of International Preliminary Report on Patentability dated Jul. 5, 2018 together with the Written Opinion received in related International Application No. PCT/JP2015/086397.

* cited by examiner

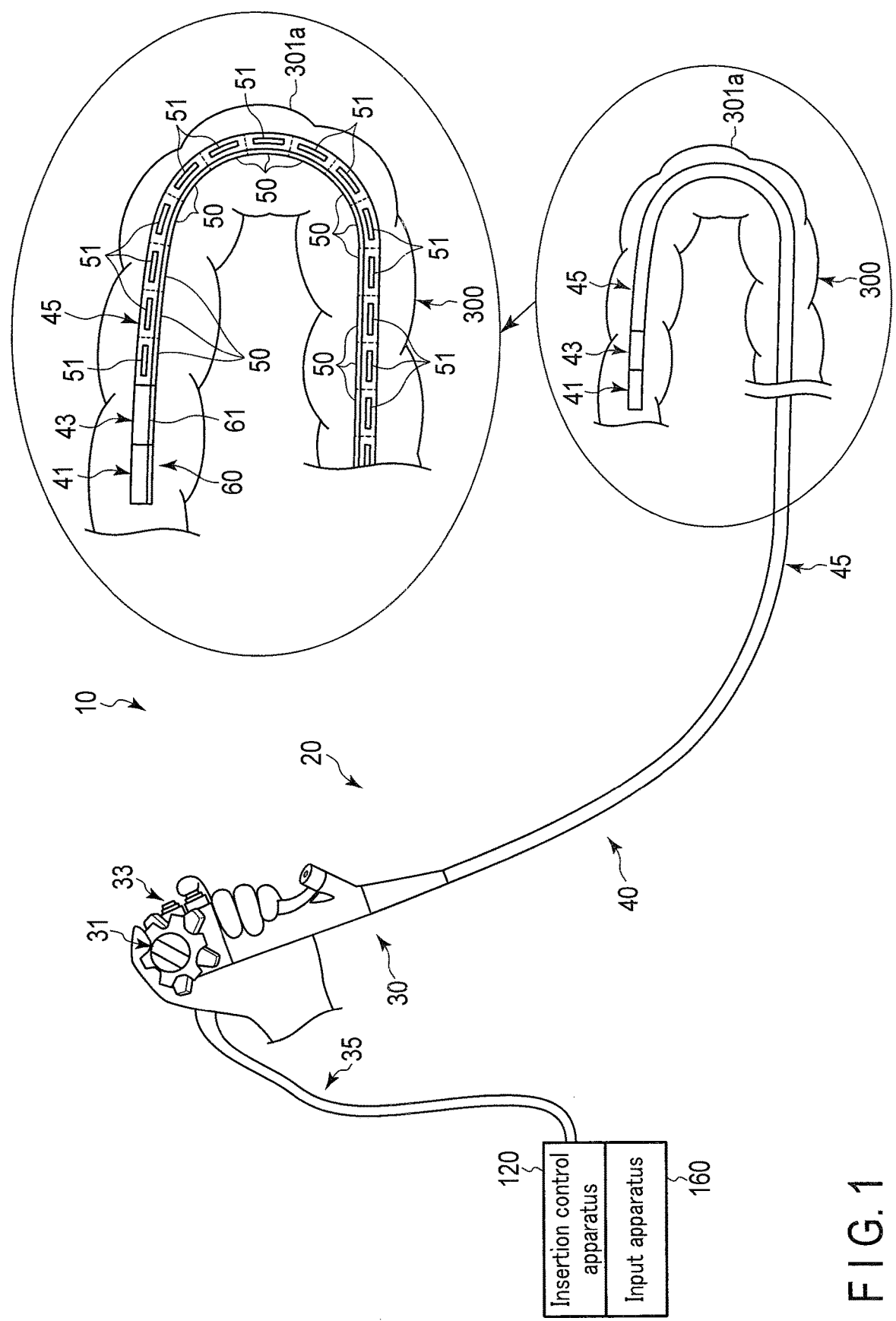
F I G. 1

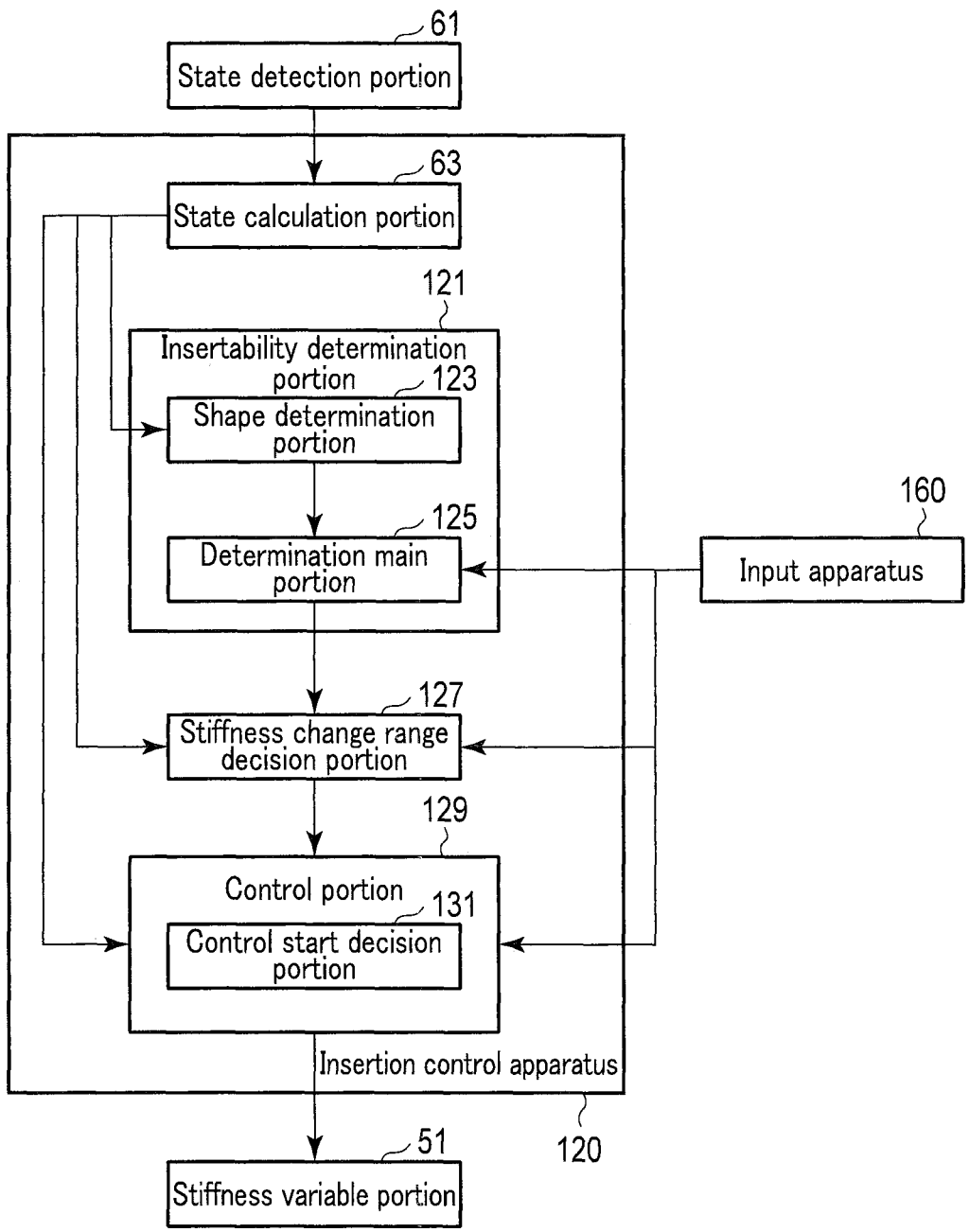
F I G. 2

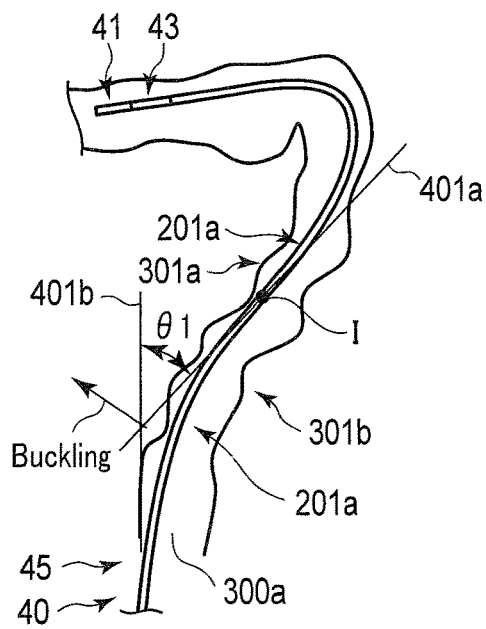
F I G. 7C
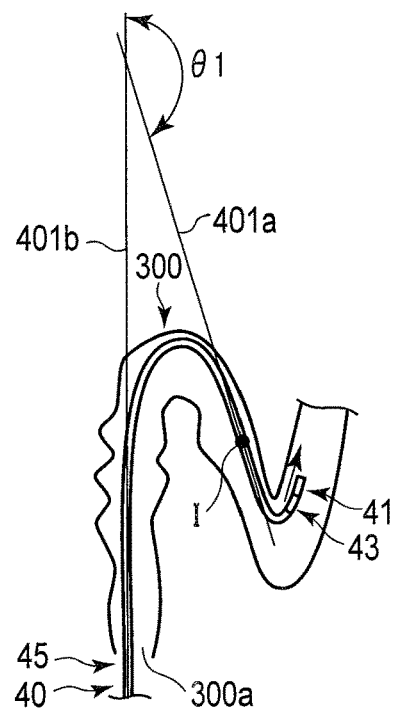
F I G. 7D

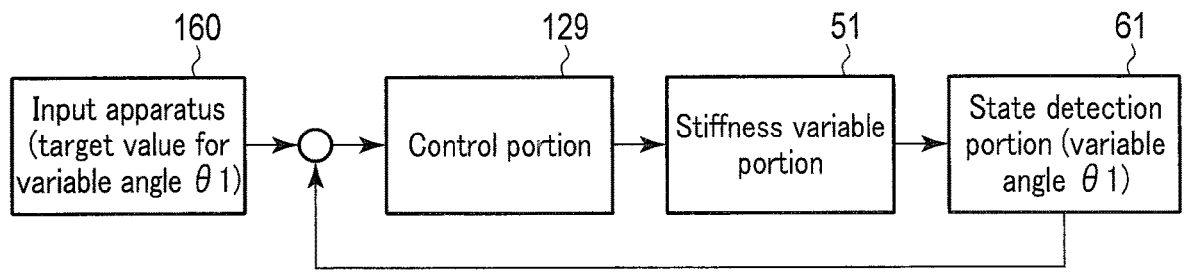
F I G. 9A
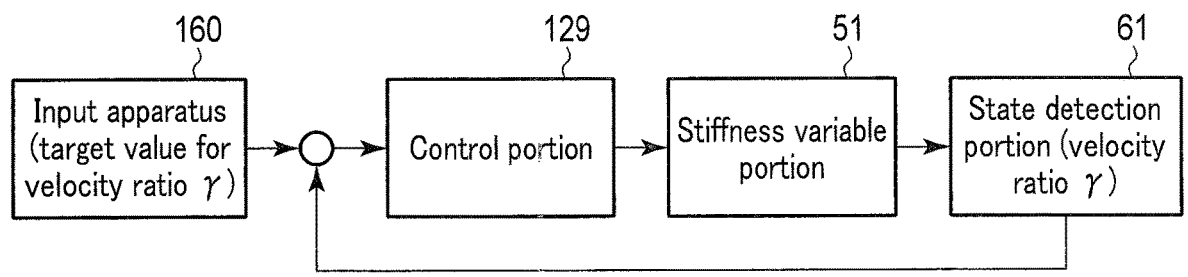
F I G. 9B
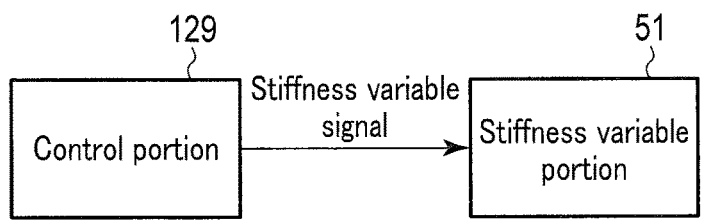
F I G. 9C

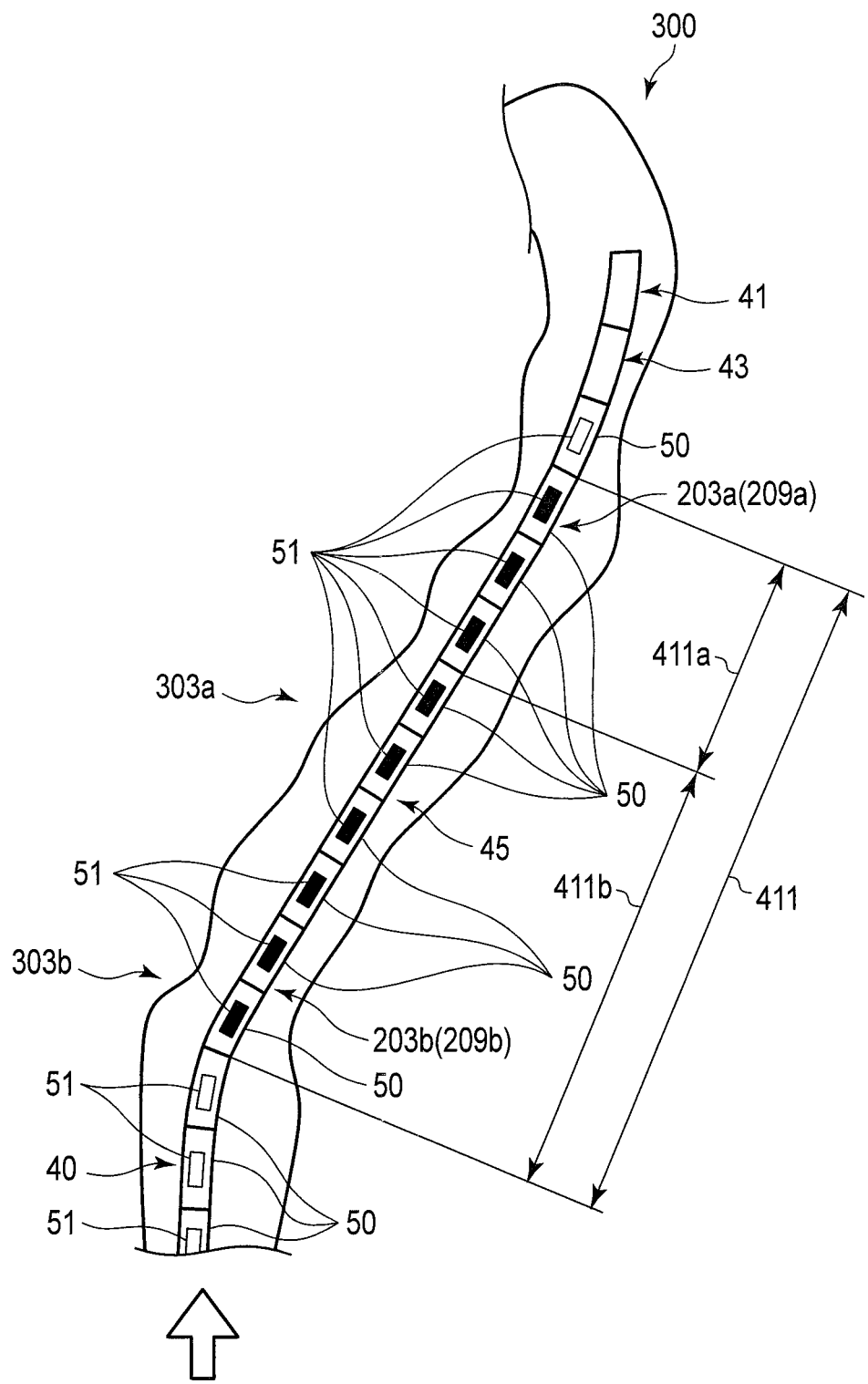
F I G. 10B

FLEXIBLE TUBE INSERTION APPARATUS

CROSS-REFERENCE TO RELATED APPLICATIONS

This application is a Continuation Application of PCT Application No. PCT/JP2015/086397, filed Dec. 25, 2015, the entire contents of which are incorporated herein by references.

BACKGROUND OF THE INVENTION

1. Field of the Invention

The present invention relates to a flexible tube insertion apparatus.

2. Description of the Related Art

As shown in FIG. 11, when an insertion section 600 inserted into a tube portion 500 (e.g., large intestine) passes through a bent portion 501 of the tube portion 500, an operator, for example, grips a proximal end portion of the insertion section 600 exposed from the large intestine to the outside of the large intestine, and pushes the insertion section 600 forward from the gripped part. For example, if the push operation is performed in a state where a distal end of the insertion section 600 has passed through the sigmoid colon, which is not fixed within the abdominal cavity, the large intestine moves freely by the push operation. As such, the insertion section 600 sometimes buckles in an S-shape, as shown in FIG. 11. Such buckling prevents the hand side force from being easily transmitted to the distal end portion of the insertion section 600, and the distal end portion is prevented from being easily inserted (advancing) toward a deep portion. The distal end portion loses a propulsion force (becomes stuck). Namely, the insertability decreases. The deep portion refers to a position ahead of the current position in the insertion direction.

In the stuck state, the operator applies an operation including at least one of a push operation, a pull operation, or a twist operation to the insertion section, to change a buckling part of the insertion section into a substantially straight shape (linearization). Thereby, the stuck state is avoided. However, the linearization is a technique hard to acquire.

For example, in the insertion section disclosed in Jpn. Pat. Appln. KOKOKU Publication No. 61-37931, the insertion section is divided into a plurality of segments in a longitudinal direction of the insertion section, and each segment has a different bending stiffness. Thereby, the patient's distress is reduced, and the insertability into a deep portion is improved.

BRIEF SUMMARY OF THE INVENTION

One embodiment of the present invention is a flexible tube insertion apparatus comprising an insertion section that comprises a distal end and a proximal end and is inserted into a subject from the distal end, a plurality of stiffness variable portions that are provided along a longitudinal direction of the insertion section, and are capable of changing a bending stiffness of the insertion section in a position where the plurality of stiffness variable portions are provided, a detector that detects shape information indicating a shape of the insertion section, at least one circuit that determines, based on the shape information, whether an S-shape that includes a first bent part forming an arc shape and a second bent part forming an arc shape and located distally on the first bent part with an inflection point between the first bent part and the second bent part is formed in the insertion section, determines whether an intersection angle between an extension line of a central axis of the insertion section located proximally on the first bent part and a tangential line for the insertion section at the inflection point is enlarged or not based on the shape information, and determines whether or not the stiffness variable portions are provided in a position of the S-shape in the insertion section when it is determined that the S-shape is formed in the insertion section and the intersection angle is enlarged, and a stiffness controller that performs control that increases a stiffness of the stiffness variable portions included in the position of the S-shape in the insertion section, if it is determined that the stiffness variable portions are provided in the position of the S-shape in the insertion section.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic diagram of a flexible tube insertion apparatus according to a first embodiment of the present invention.

FIG. 2 is a diagram illustrating a relationship among a state detection portion, a state calculation portion, an insertability determination portion, a stiffness change range decision portion, a stiffness control portion, a stiffness variable portion, and an input apparatus.

FIG. 7C is a diagram showing an example of a state where the determination main portion determines that the insertability of the insertion section is decreased due to buckling.

FIG. 7D is a diagram showing an example of a state where the determination main portion determines that the insertability of the insertion section is not decreased due to buckling.

FIG. 9A is a diagram showing that the stiffness control portion performs feedback control so that a variable angle is adjusted to a preset target value.

FIG. 9B is a diagram showing that the stiffness control portion performs feedback control so that a velocity ratio is adjusted to a preset target value.

FIG. 9C is a diagram showing that the stiffness control portion performs open control.

FIG. 10B is a diagram showing a state where the stiffness of the stiffness variable portion shown in FIG. 10A is controlled.

DETAILED DESCRIPTION

Figure 3:
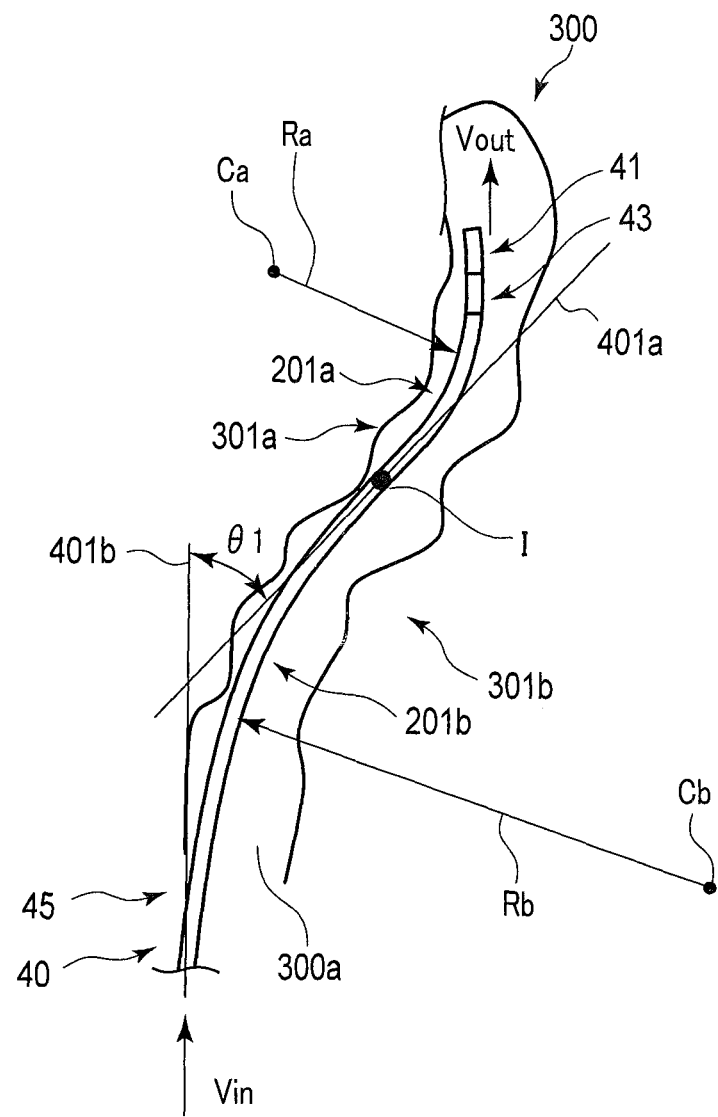
FIG. 3 is a diagram showing bending information detected by a detection unit.

Hereinafter, embodiments of the present invention will be described in detail with reference to the accompanying drawings. In FIG. 1, illustration of a state calculation portion 63 is omitted. Likewise, in some of the drawings, illustration of some members is omitted for clarification of the illustration. The deep portion refers to a position ahead of the current position as viewed in the insertion direction of an insertion section 40.

First Embodiment

[Configuration]
An explanation will now be given of the first embodiment, with reference to the accompanying drawings.

[Flexible Tube Insertion Apparatus (Hereinafter Referred to as an Insertion Apparatus 10)]

An insertion apparatus 10, which is an endoscope apparatus as shown in FIG. 1, is installed in, for example, an operation room or an examination room. The insertion apparatus 10 includes an endoscope 20 for medical use, an insertion control apparatus 120, and an input apparatus 160 connected to the insertion control apparatus 120. The insertion apparatus 10 includes a light source apparatus (not shown in the drawings) connected to the endoscope 20, an image control apparatus (not shown in the drawings) connected to the endoscope 20, and a display apparatus (not shown in the drawings) connected to the image control apparatus.

The endoscope 20 is an example of an insertion apparatus that is inserted into a subject including a tube portion 300, such as the large intestine. The endoscope 20 images the inside of the tube portion 300 using an image sensor of an imaging unit, not shown. The image sensor includes, for example, a CCD.

The light source apparatus that is not shown emits light to allow the image sensor to perform imaging. The light is guided to an illumination portion, not shown, of the illumination unit by a light guide member, not shown, of the illumination unit provided in the endoscope 20. The light is emitted from the illumination portion toward the outside as illumination light. An image taken by the image sensor is output to the image control apparatus, not shown, from the image sensor via a signal line of the imaging unit provided inside the endoscope 20.

The image control apparatus that is not shown processes a signal in such a manner that the image taken by the image sensor is displayed on the display apparatus, not shown.

The insertion control apparatus 120 controls the bending stiffness of the insertion section 40 arranged in the endoscope 20. The details thereof will be described later.

The display apparatus that is not shown in the drawings displays an image taken by the image sensor and image-processed by the image control apparatus (not shown in the drawings). The display apparatus that is not shown in the drawings is connected to the image control apparatus (not shown in the drawings) via a cable (not shown in the drawings). The image control apparatus includes, for example, a CPU. The display apparatus includes, for example, a monitor.

The input apparatus 160 is used to input various start instructions that will be described later.

[Endoscope 20]

The endoscope 20 will be explained as a medical flexible endoscope, for example, but is not limited thereto. The endoscope 20 may be, for example, a flexible endoscope for industrial use. A catheter, a treatment instrument, or the like may be used instead of the endoscope 20. The endoscope 20, a catheter, a treatment instrument, or the like is only required to include a flexible insertion section 40 to be inserted into a subject. The subject is not limited to, for example, a human, and may be an animal or any other structural object. The endoscope 20 may be a front-viewing endoscope 20, or a side-viewing endoscope 20.

The endoscope 20 includes an operation section 30 to be gripped by the operator and the insertion section 40 to be inserted into the subject.

The operation section 30 is continuous with the proximal end portion of the insertion section 40. The operation section 30 includes a bending operation portion 31 used to operate a bendable portion 43, which will be described later, and a switch portion 33 used to operate respective units such as an imaging unit. The operation section 30 further includes a universal cord 35, and is connected, via the universal cord 35, to the light source apparatus that is not shown, the image control apparatus that is not shown, and the insertion control apparatus 120.

The insertion section 40 is tubular, elongated, and flexible. The insertion section 40 advances toward and retreats from the tube portion 300 inside the tube portion 300. The insertion section 40 is bendable according to an internal shape of the tube portion 300. The insertion section 40 includes a distal rigid portion 41, a bendable portion 43, and a flexible tube 45 in this order from the distal end portion of the insertion section 40 toward the proximal end portion of the insertion section 40. A proximal end portion of the distal rigid portion 41 is coupled to a distal end portion of the bendable portion 43, a proximal end portion of the bendable portion 43 is coupled to a distal end portion of the flexible tube 45, and a proximal end portion of the flexible tube 45 is coupled to the operation section 30. The image sensor and the illumination portion described above are provided inside the distal rigid portion 41.

[Segments 50]

As shown in FIG. 1, the flexible tube 45 of the insertion section 40 is divided into a plurality of segments 50 arranged in a column shape along the longitudinal axis direction of the insertion section 40. The segments 50 may function as non-existent virtual areas, or may function as existent structures.

The bending stiffness of each segment 50 can be independently changed under control of a control portion 129 (see FIG. 2), which will be described later, arranged in the insertion control apparatus 120. The bending stiffness of the flexible tube 45 may be partially changed by the bending stiffness of the respective segments 50 independently controlled by the control portion 129.

The segments 50 are obtained by dividing the flexible tube 45, but are not limited thereto. The segments 50 may be obtained by dividing the insertion section 40. It is thereby possible to partially change the bending stiffness of the insertion section 40 based on the bending stiffness of each of the segments 50 independently controlled by the control portion 129.

[Stiffness Variable Portion 51]

As shown in FIG. 1, the insertion apparatus 10 includes one or more stiffness variable portions 51, the stiffness of which is variable. The stiffness variable portions 51 are incorporated into the respective segments 50. The stiffness variable portions 51 may be incorporated into all of the segments 50, or may be incorporated into only some of the segments 50. The area at which the stiffness variable portion 51 is provided may function at least as the segment 50. One stiffness variable portion 51 may be integrally incorporated into a plurality of segments 50. The stiffness variable portions 51 may be arranged in a line along the longitudinal axis direction of the insertion section 40, or may be arranged in a plurality of lines. When the stiffness variable portions 51 are arranged in a plurality of lines, the stiffness variable portions 51 may be provided at the same position in such a manner that the stiffness variable portions 51 are adjacent to each other as viewed in the circumferential direction of the flexible tube 45, or may be provided so as to be shifted as viewed in the longitudinal axis direction of the insertion section 40. The stiffness variable portions 51 are only required to change the bending stiffness of the insertion section 40 in units of segments, according to a change in stiffness of the stiffness variable portions 51.

Although not shown in the drawings, the stiffness variable portion 51 is configured by an actuator including, for example, a coil pipe formed by a metal line and a conductive electroactive polymer artificial muscle (hereinafter referred to as EPAM) enclosed inside the coil pipe. The central axis of the coil pipe is provided to match the central axis of the insertion section 40, or in parallel therewith. The coil pipe includes electrodes provided on both end portions of the coil pipe.

The electrodes are connected to the control portion 129 via a signal cable (not shown in the drawings) incorporated into the endoscope 20, and receive electric power supplied from the control portion 129. When a voltage is applied to the EPAM via the electrodes, the EPAM extends and contracts along the central axis of the coil pipe. However, the EPAM is restricted from extending and contracting by the coil pipe. Thereby, the stiffness of the stiffness variable portions 51 changes. The stiffness of the stiffness variable portions 51 increases as the value of the applied voltage increases. When the stiffness of the stiffness variable portion 51 changes, the bending stiffness of the segments 50 incorporating the stiffness variable portions 51 also changes in accordance therewith. Electric power is independently supplied to the respective electrodes. Accordingly, the stiffness variable portions 51 independently change in stiffness, and the segments 50 also independently change in bending stiffness. In this manner, the stiffness variable portions 51 change the bending stiffness of the segments 50 according to the change in stiffness of the stiffness variable portions 51, and partially change the bending stiffness of the flexible tube 45 according to the change in bending stiffness of the segments 50.

As the stiffness variable portion 51, a shape memory alloy may be used, instead of the EPAM.

[Detection Unit 60]

As shown in FIGS. 1 and 2, the insertion apparatus 10 includes a detection unit 60 that detects state information of the insertion section 40 including at least shape information of the insertion section 40. The detection unit 60 starts detection upon receiving detection operation start instructions (a detection start instruction and a calculation start instruction, which will be described later) input from the input apparatus 160, and constantly performs the detection. The detection timing may be every predetermined elapse of time, and is not particularly limited.

The detection unit 60 includes a state detection portion 61 arranged in the insertion section 40, as shown in FIG. 1, and a state calculation portion 63 arranged in the insertion control apparatus 120, as shown in FIG. 2.

The state detection portion 61 is arranged alongside the stiffness variable portions 51. The state detection portion 61 detects state information of the insertion section 40 including one of shape information, twist information, or position information of the insertion section 40, or two or more of these pieces of information. The shape information of the insertion section 40 indicates, for example, the shape of the insertion section 40 as viewed in the longitudinal axis direction of the insertion section 40. Examples of the state detection portion 61 include a magnetism generation means, an optical fiber sensor, a strain sensor, and absorption member.

The state detection portion 61 constantly performs a detection (operation) after the detection start instruction output from the input apparatus 160 is input to the state detection portion 61. The state detection portion 61 is connected to the state calculation portion 63 by wire or wirelessly, for example, and the detection result detected by the state detection portion 61 is output to the state calculation portion 63.

Figure 8A:
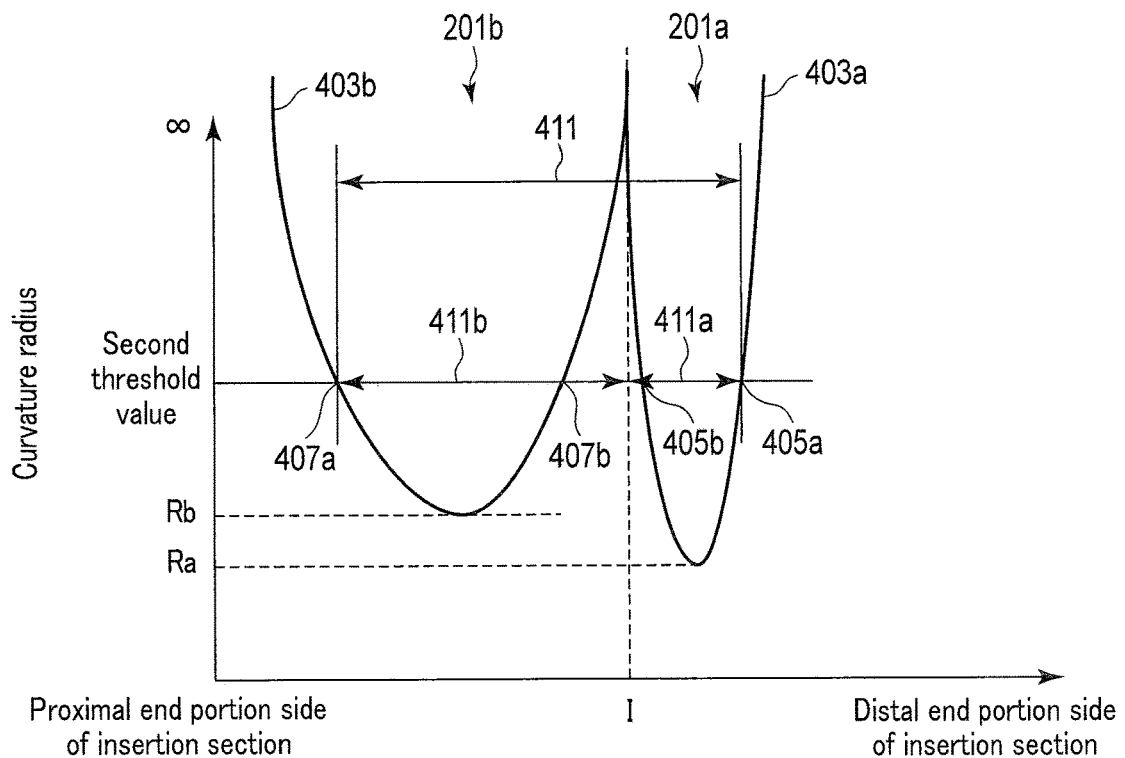
FIG. 8A is a diagram showing an example of a state where the stiffness change range decision portion decides a range of a stiffness change.
Figure 8B:
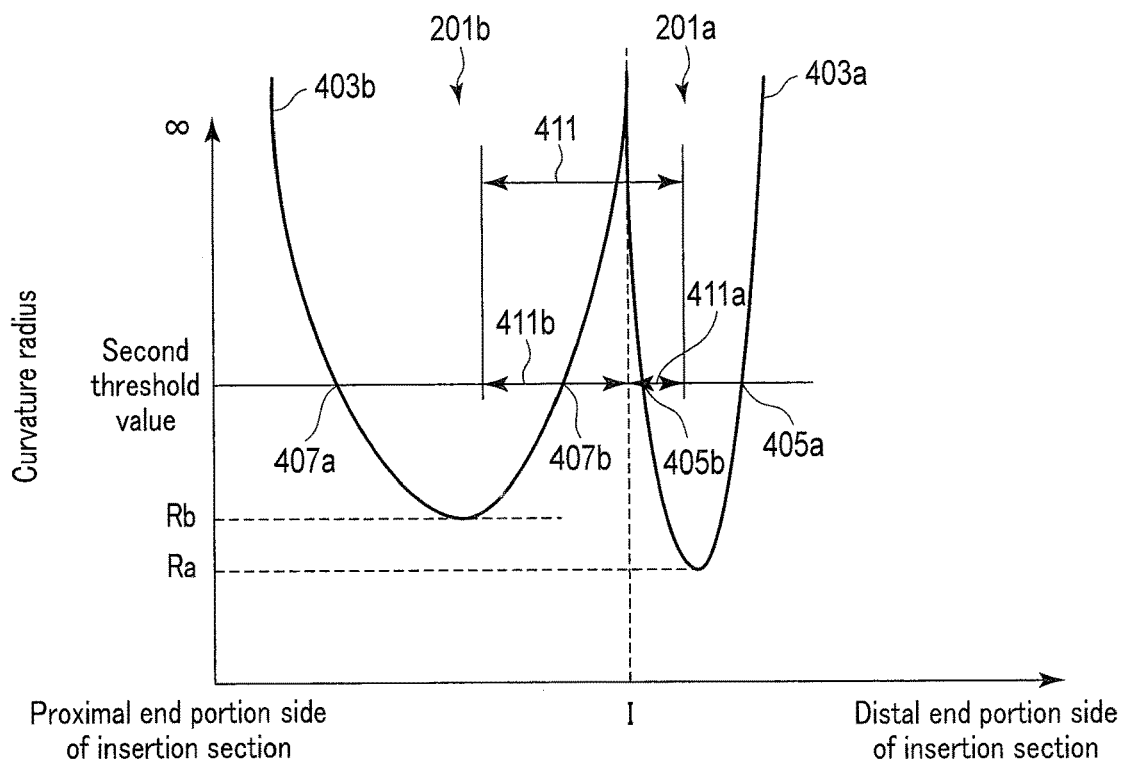
FIG. 8B is a diagram showing an example of a state where the stiffness change range decision portion decides a range of a stiffness change.

The state calculation portion 63 calculates state information of the insertion section 40 on the basis of the detection result of the state detection portion 61. The state information of the insertion section 40 calculated by the state calculation portion 63 includes, for example, the shape information, twist information, and position information of the insertion section 40. As shown in FIG. 3, the state information of the insertion section 40 calculated by the state calculation portion 63 includes, for example: two bent parts 201a and 201b that are continuous with each other in the insertion section 40; an inflection point I; curvature radii Ra and Rb of the bent parts 201a and 201b, respectively; curvature centers Ca and Cb of the bent parts 201a and 201b, respectively; and a variable angle θ1. In the explanation that follows, let us assume that the bent part 201a is located ahead of the bent part 201b as viewed in the insertion direction of the insertion section 40. The bent parts 201a and 201b that are continuous with each other represent s-shaped parts of the insertion section 40. The inflection point I is a connection part between the bent part 201a and the bent part 201b, and is one point at which the curvature radius of the bent part between the bent part 201a and the bent part 201b is ∞. The bent parts 201a and 201b are arranged with the inflection point I between them. The variable angle θ1 represents an angle formed between a tangential line 401a of the inflection point I, and an extension line 401b of the central axis of a part of the insertion section 40 located at an entrance 300a of the tube portion 300. Also, the state information of the insertion section 40 calculated by the state calculation portion 63 includes, for example, bend curves 403a and 403b representing a relationship between the bent parts 201a and 201b and the curvature radii Ra and Rb of the bent parts 201a and 201b, as shown in FIGS. 8A and 8B. The state information of the insertion section 40 calculated by the state calculation portion 63 includes velocity information of the insertion section 40 calculated based on the position information of the insertion section 40 and time. The velocity information includes a distal velocity Vout of the distal end portion of the insertion section 40, a proximal velocity Vin on the proximal end portion side (hand side) of the insertion section 40, and a velocity ratio γ between the distal velocity Vout and the proximal velocity Vin (distal velocity Vout/proximal velocity Vin), as shown in FIG. 3. The state calculation portion 63 is configured by, for example, an arithmetic circuit including a CPU, an ASIC, or the like.

The state calculation portion 63 constantly performs a calculation (operation) after the calculation start instruction output from the input apparatus 160 is input to the state calculation portion 63, in a state where a detection result of the state detection portion 61 has been input. The detection timing may be every predetermined elapse of time, and is not particularly limited. The state calculation portion 63 is connected to the display apparatus (not shown in the drawings), and outputs a calculation result calculated by the state calculation portion 63 to the display apparatus. As shown in FIG. 3, the display apparatus (not shown in the drawings) displays the current state information of the insertion section 40 in the tube portion 300, on the basis of the calculation result calculated by the state calculation portion 63. The display is performed in a three-dimensional manner, for example. The operator is capable of monitoring the position and the state of the insertion section 40 in the tube portion 300 on the basis of the state information of the insertion section 40 displayed on the display apparatus.

The state calculation portion 63 is connected to an insertability determination portion (hereinafter referred to as a determination portion 121), a stiffness change range decision portion (hereinafter referred to as a first decision portion 127), and a stiffness control portion (hereinafter referred to as a control portion 129), which will be described below, and outputs the calculation result calculated by the state calculation portion 63 to the determination portion 121, the first decision portion 127, and the control portion 129.

[Determination Portion 121]

The insertion apparatus 10 includes a determination portion 121 that determines whether the insertability of the insertion section 40 into a deep portion from the current position is decreased or not, based on the state information of the insertion section 40, as shown in FIG. 2. This insertability represents the advancing capability of the insertion section 40, namely, the propulsion capability of the insertion section 40. The part of the insertion section 40 on which the determination portion 121 performs the determination includes the bent parts 201a and 201b. The part is a part of the insertion section 40 that is located within a desired range when the state calculation portion 63 calculates the shape of the insertion section 40. The determination portion 121 determines whether the insertability is decreased or not, based on the bent parts 201a and 201b. The determination portion 121 is arranged in the insertion control apparatus 120. The determination portion 121 is configured by, for example, an arithmetic circuit including a CPU, an ASIC, or the like.

The determination portion 121 includes: a shape determination portion 123 that determines the shape of the insertion section 40 based on the state information (inflection point I, curvature radii Ra and Rb, and curvature centers Ca and Cb) of the insertion section 40 output from the state calculation portion 63; and a determination main portion 125 that determines a decrease of the insertability of the insertion section 40 due to buckling based on the state information (variable angle θ1 and curvature radii Ra and Rb) of the insertion section 40 output from the state calculation portion 63 and a result of the determination of the shape determination portion 123. The shape determination portion 123 starts determination when a determination start instruction is input from the input apparatus 160, and constantly performs the determination. The determination timing may be every predetermined elapse of time, and is not particularly limited. The determination main portion 125 performs determination when a result of the determination of the shape determination portion 123 is input.

Figure 4A:
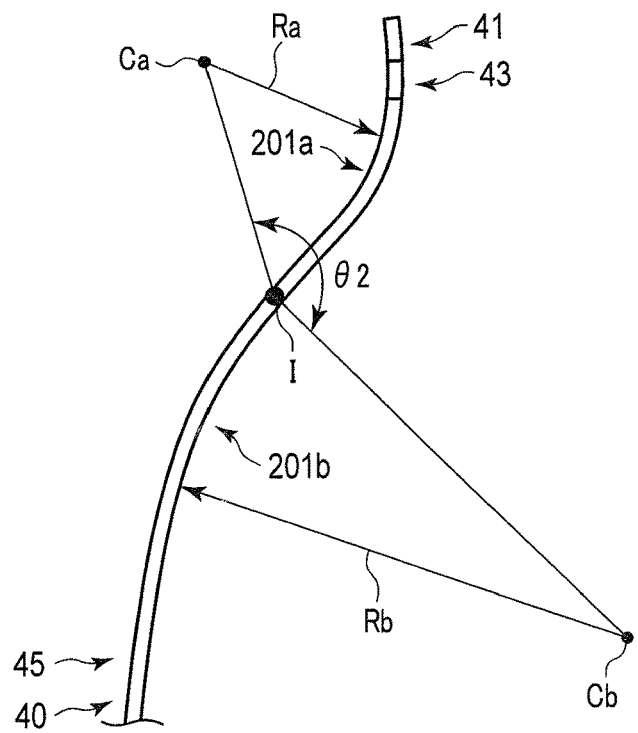
FIG. 4A is a diagram showing a state where a shape determination portion of the insertability determination portion determines that a shape of an insertion section is an S-shape based on an angle.
Figure 4B:
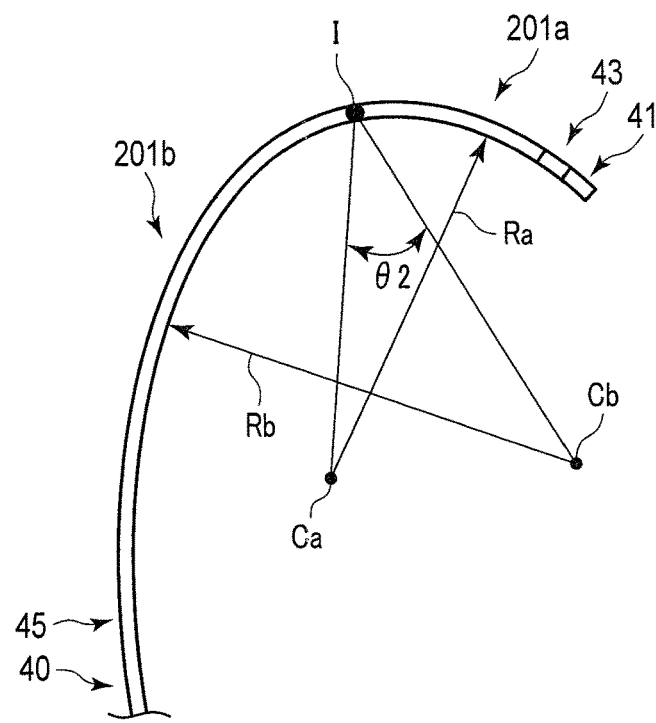
FIG. 4B is a diagram showing a state where the shape determination portion determines that the shape of the insertion section is not an S-shape based on an angle.

The shape determination portion 123 calculates, as angle θ2, an angle formed by a line segment that connects the curvature center Ca, the inflection point I, and the curvature center Cb, as shown in FIGS. 4A and 4B. The shape determination portion 123 outputs the calculation result to the control portion 129. The shape determination portion 123 also determines whether the shape of the insertion section 40 is an S-shape or not based on the angle θ2. For example, the shape determination portion 123 determines that the shape of the insertion section 40 is an S-shape if the angle is θ2>90°, as shown in FIG. 4A, and determines that the shape of the insertion section 40 is not an S-shape if the angle is θ2<90°, as shown in FIG. 4B.

The shape determination portion 123 may perform determination as described below.

Figure 5A:
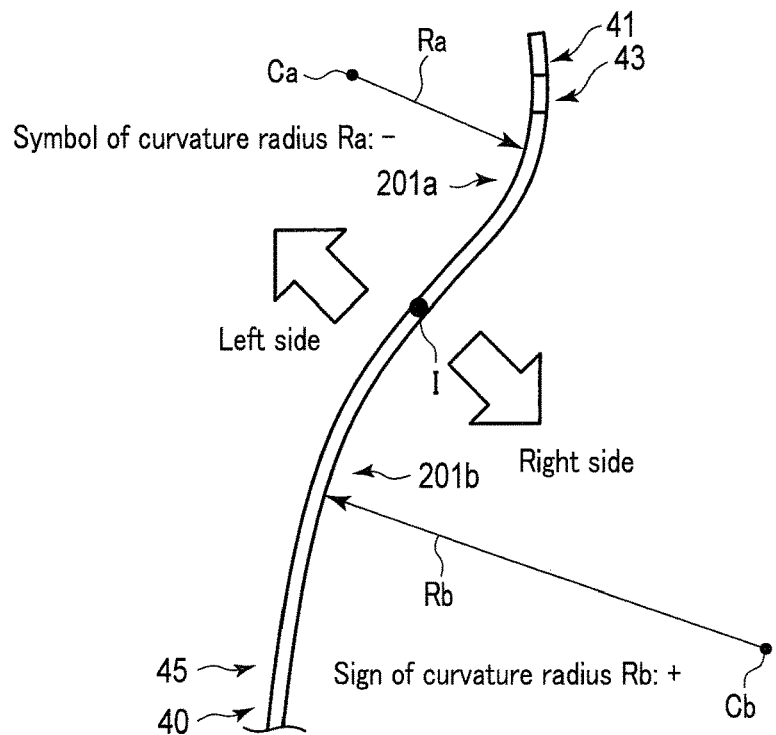
FIG. 5A is a diagram showing a state where the shape determination portion determines that the shape of the insertion section is an S-shape based on a sign defined for a radius of curvature.
Figure 5B:
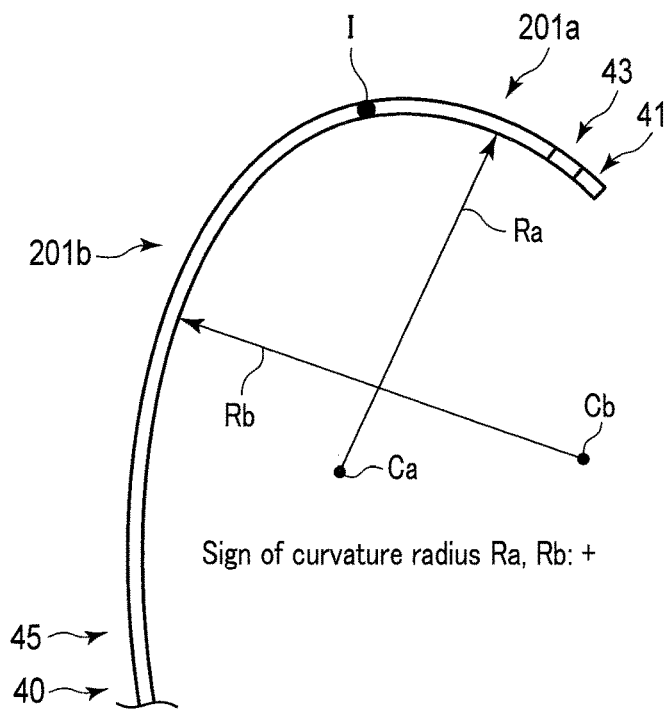
FIG. 5B is a diagram showing a state where the shape determination portion determines that the shape of the insertion section is not an S-shape based on a sign defined for a radius of curvature.

For example, the shape determination portion 123 defines, as "+," the sign of the curvature radius of the bent part that is located on one side (right side) of the insertion section 40 including the inflection point I as viewed in the insertion direction of the insertion section 40, as shown in FIGS. 5A and 5B. To briefly explain, the shape determination portion 123 defines, as "+," the sign of the curvature radius of the bent part that is located on the right side (one side) of the insertion section 40. The shape determination portion 123 defines, as "−," the sign of the curvature radius of the bent part that is located on the other side (left side) of the insertion section 40 including the inflection point I as viewed in the insertion direction of the insertion section 40. To briefly explain, the shape determination portion 123 defines, as "−," the sign of the curvature radius of the bent part that is located on the left side (the other side) of the insertion section 40. The shape determination portion 123 determines whether the shape of the insertion section 40 is an S-shape or not based on the signs defined for the curvature radii Ra and Rb.

For example, the shape determination portion 123 determines that the shape of the insertion section 40 is an S-shape if the sign of the curvature radius Ra is "−" and the sign of the curvature radius Rb is "+," as shown in FIG. 5A. Alternatively, the shape determination portion 123, for example, determines that the shape of the insertion section 40 is an S-shape if the sign of the curvature radius Ra is "+" and the sign of the curvature radius Rb is "−," which is not shown in the drawings. In this manner, the shape determination portion 123 determines that the shape of the insertion section 40 is an S-shape if the signs of the curvature radii Ra and Rb are different from each other.

For example, the shape determination portion 123 determines that the shape of the insertion section 40 is not an S-shape if the sign of the curvature radius Ra is "+" and the sign of the curvature radius Rb is "+," as shown in FIG. 5B. Alternatively, the shape determination portion 123, for example, determines that the shape of the insertion section 40 is not an S-shape if the sign of the curvature radius Ra is "−" and the sign of the curvature radius Rb is "−," which is not shown in the drawings. In this manner, the shape determination portion 123 determines that the shape of the insertion section 40 is not an S-shape if the signs of the curvature radii Ra and Rb are the same.

The shape determination portion 123 may define, as a first area, an area located on the right side (one side) of the insertion section 40 including the inflection point I, and define, as a second area, an area located on the left side (the other side) of the insertion section 40 including the inflection point I, instead of defining the signs. For example, the shape determination portion 123 may use the curvature centers Ca and Cb instead of the curvature radii Ra and Rb. If the curvature centers Ca and Cb are used, "+" and "−" may be defined, as described above. The shape determination portion 123 may determine whether the shape of the insertion section 40 is an S-shape or not based on the position of the arrangement of the curvature centers Ca and Cb with respect to the first and second areas. In this case, the shape determination portion 123 determines that the shape of the insertion section 40 is an S-shape if the curvature centers Ca and Cb are arranged indifferent areas, and determines that the shape of the insertion section 40 is not an S-shape if the curvature centers Ca and Cb are arranged in the same area.

Alternatively, the shape determination portion 123 may perform determination as described below.

Figure 6A:
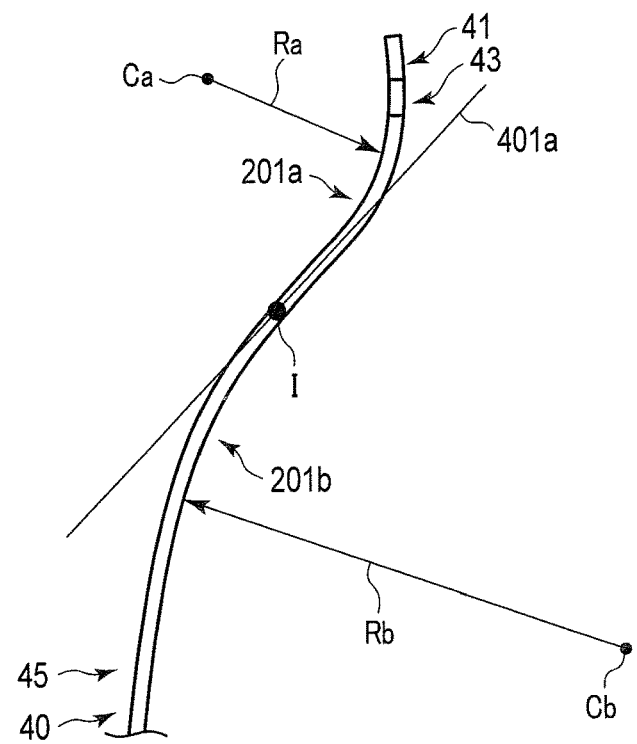
FIG. 6A is a diagram showing a state where the shape determination portion determines that the shape of the insertion section is an S-shape based on a position of a center of curvature with respect to a tangential line of an inflection point.
Figure 6B:
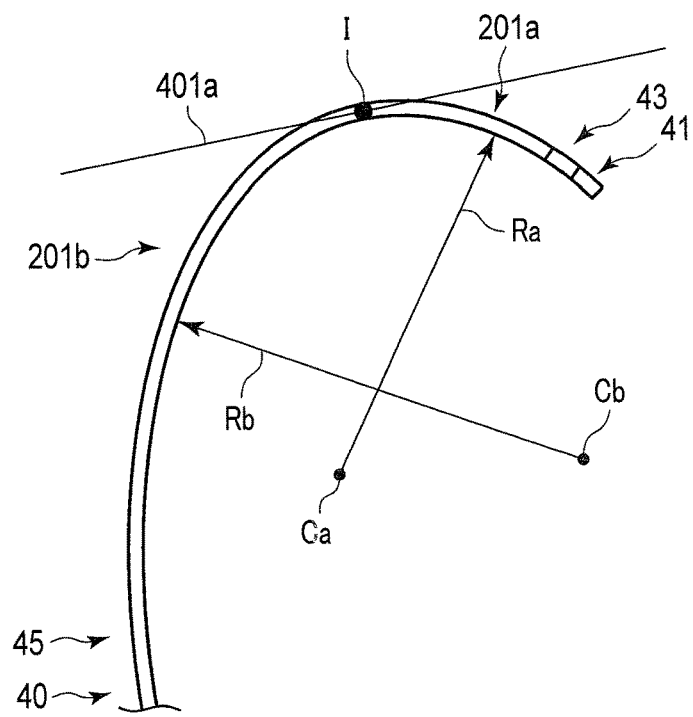
FIG. 6B is a diagram showing a state where the shape determination portion determines that the shape of the insertion section is not an S-shape based on a position of a center of curvature with respect to a tangential line of an inflection point.

For example, the shape determination portion 123 may determine whether the shape of the insertion section 40 is an S-shape or not based on the positions of the respective curvature centers Ca and Cb with respect to the tangential line 401a of the inflection point I, as shown in FIGS. 6A and 6B. The shape determination portion 123 determines on which side the curvature centers Ca and Cb are respectively arranged relative to the tangential line 401a. Next, the shape determination portion 123 determines that the shape of the insertion section 40 is an S-shape if the curvature center Ca is arranged across the tangential line 401a from the curvature center Cb, as shown in FIG. 6A. For example, the shape determination portion 123 determines that the shape of the insertion section 40 is not an S-shape if the curvature center Ca is arranged on the same side as the curvature center Cb relative to the tangential line 401a, as shown in FIG. 6B.

In this manner, the shape determination portion 123 determines whether the bent parts 201a and 201b are bent in the same direction or not. The shape determination portion 123 outputs the determination result to the determination main portion 125.

Figure 7A:
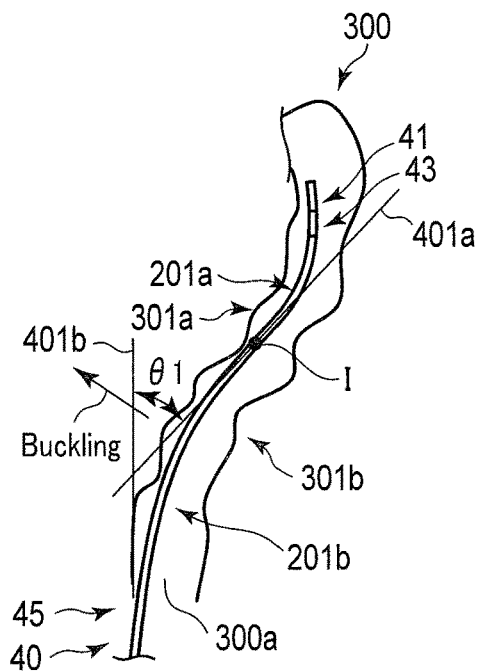
FIG. 7A is a diagram showing an example of a state where a determination main portion of the insertability determination portion determines that the insertability of the insertion section is decreased due to buckling.
Figure 7B:
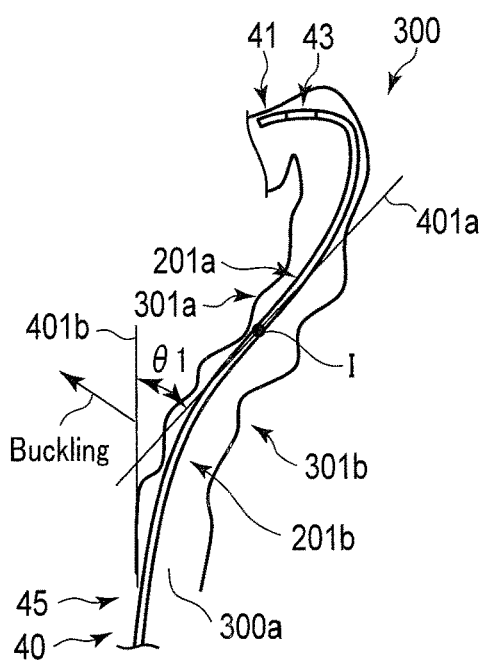
FIG. 7B is a diagram showing an example of a state where the determination main portion determines that the insertability of the insertion section is decreased due to buckling.

The state information (variable angle θ1) of the insertion section 40 output from the state calculation portion 63 and the result of the determination by the shape determination portion 123 that the shape of the insertion section 40 is an S-shape are input to the determination main portion 125. As shown in FIGS. 7A, 7B, and 7C, the determination main portion 125 determines whether or not the insertion section 40 is buckled, namely, determines whether or not the insertion section 40 is inserted into a deep portion by being pushed. The determination main portion 125 determines that the insertability of the insertion section 40 is decreased by buckling when the shape determination portion 123 determines that the shape of the insertion section 40 is an S-shape, and when the variable angle θ1 is equal to or less than a first threshold value and dθ/dt>0. The relationship dθ/dt>0 indicates that the temporal change of the variable angle θ1 is positive. The first threshold value is, for example, 40°. For example, in FIG. 7D, the shape of the insertion section 40 is an S-shape, but the variable angle θ1 is equal to or greater than the first threshold value. Therefore, the determination main portion 125 does not determine that the insertability is decreased by buckling.

The curvature radii Ra and Rb may be input from the state calculation portion 63 to the determination main portion 125, as the state information of the insertion section 40. In this case, the determination main portion 125 determines that the insertability of the insertion section 40 is decreased by buckling when the shape determination portion 123 determines that the shape of the insertion section 40 is an S-shape, and when the variable angle 91 is equal to or less than the first threshold value and Rb/dt<0. The relationship Rb/dt<0 indicates that the temporal change of the curvature radius Rb on the hand side is negative.

The determination main portion 125 outputs the determination result to the first decision portion 127. The determination main portion 125 further outputs, to the first decision portion 127, information that the parts of the insertion section 40 used for the determination by the determination main portion 125 are the bent parts 201a and 201b.

[First Decision Portion 127]

As shown in FIGS. 2 and 8A, the insertion apparatus 10 includes the first decision portion 127 that decides a stiffness change range 411 in apart of the insertion section 40 used for the determination by the determination main portion 125 when the determination main portion 125 of the determination portion 121 determines that the insertability of the insertion section 40 is decreased. For example, the parts of the insertion section 40 used for the determination by the determination main portion 125 include the bent parts 201a and 201b output from the state calculation portion 63. For example, the parts indicate S-shaped parts of the insertion section 40. The first decision portion 127 decides the stiffness change range 411, which is a range where the bending stiffness of the bent parts 201a and 201b is changed, in order to at least partially change the bending stiffness of the respective bent parts 201a and 201b so that the insertability of the insertion section 40 is not decreased. The first decision portion 127 is arranged in the insertion control apparatus 120. The determination portion 121 is configured by, for example, an arithmetic circuit including a CPU, an ASIC, or the like.

In this context, a threshold value that is greater than the curvature radii Ra and Rb is referred to as a second threshold value.

As shown in FIG. 8A, the first decision portion 127 calculates a first distant intersection point 405a and a first close intersection point 405b, which are intersection points between the second threshold value and the bend curve 403a, in the bent part 201a based on the second threshold value and the bend curve 403a. The first distant intersection point 405a is an intersection point away from the inflection point I. The first close intersection point 405b is an intersection point close to the inflection point I, and is located between the first distant intersection point 405a and the inflection point I.

The first decision portion 127 calculates a second distant intersection point 407a and a second close intersection point 407b, which are intersection points between the second threshold value and the bend curve 403b, in the bent part 201b based on the second threshold value and the bend curve 403b. The second distant intersection point 407a is an intersection point away from the inflection point I. The second close intersection point 407b is an intersection point close to the inflection point I, and is located between the second distant intersection point 407a and the inflection point I.

For example, the first decision portion 127 decides a range from the inflection point I to the first distant intersection point 405a as a stiffness change range 411a in the bent part 201a, as shown in FIG. 8A. The first decision portion 127 decides a range from the inflection point I to the second distant intersection point 407a as a stiffness change range 411b in the bent part 201b. A combination of the stiffness change ranges 411a and 411b is the stiffness change range 411. The stiffness change range 411a is continuous with the stiffness change range 411b.

The first decision portion 127 need not decide the range from the inflection point I to the first distant intersection point 405a as the stiffness change range 411a. For example, the first decision portion 127 may decide a desired proportion of the range from the inflection point I to the first distant intersection point 405a as the stiffness change range 411a in the bent part 201a on the basis of the inflection point I, as shown in FIG. 8B. The first decision portion 127 may also decide a desired proportion of the range from the inflection point I to the second distant intersection point 407a as the stiffness change range 411b in the bent part 201b on the basis of the inflection point I. The desired proportion is, for example, 50%. If the desired proportion is 100%, the stiffness change range 411a shown in FIG. 8B is the same as the stiffness change range 411a shown in FIG. 8A. The desired proportion may be equal to or greater than 100%. The desired proportion of the stiffness change range 411a may be the same as or different from the desired proportion of the stiffness change range 411b.

The first decision portion 127 may decide the stiffness change range 411 for only one of the bent part 201a or the bent part 201b.

The first decision portion 127 starts decision when a decision start instruction is input from the input apparatus 160, and constantly performs the decision. The decision timing may be every predetermined elapse of time, and is not particularly limited.

[Control Portion 129]

As shown in FIG. 2, the insertion apparatus 10 includes a control portion 129 arranged in the insertion control apparatus 120. The control portion 129 is configured by, for example, an arithmetic circuit including a CPU, an ASIC, or the like. The control portion 129 is connected to the stiffness variable portions 51 via a signal cable, not shown, incorporated into the endoscope 20. The control portion 129 starts control upon receiving a control start instruction input from the input apparatus 160, and constantly performs the control. The control timing may be every predetermined elapse of time, and is not particularly limited.

Figure 10A:
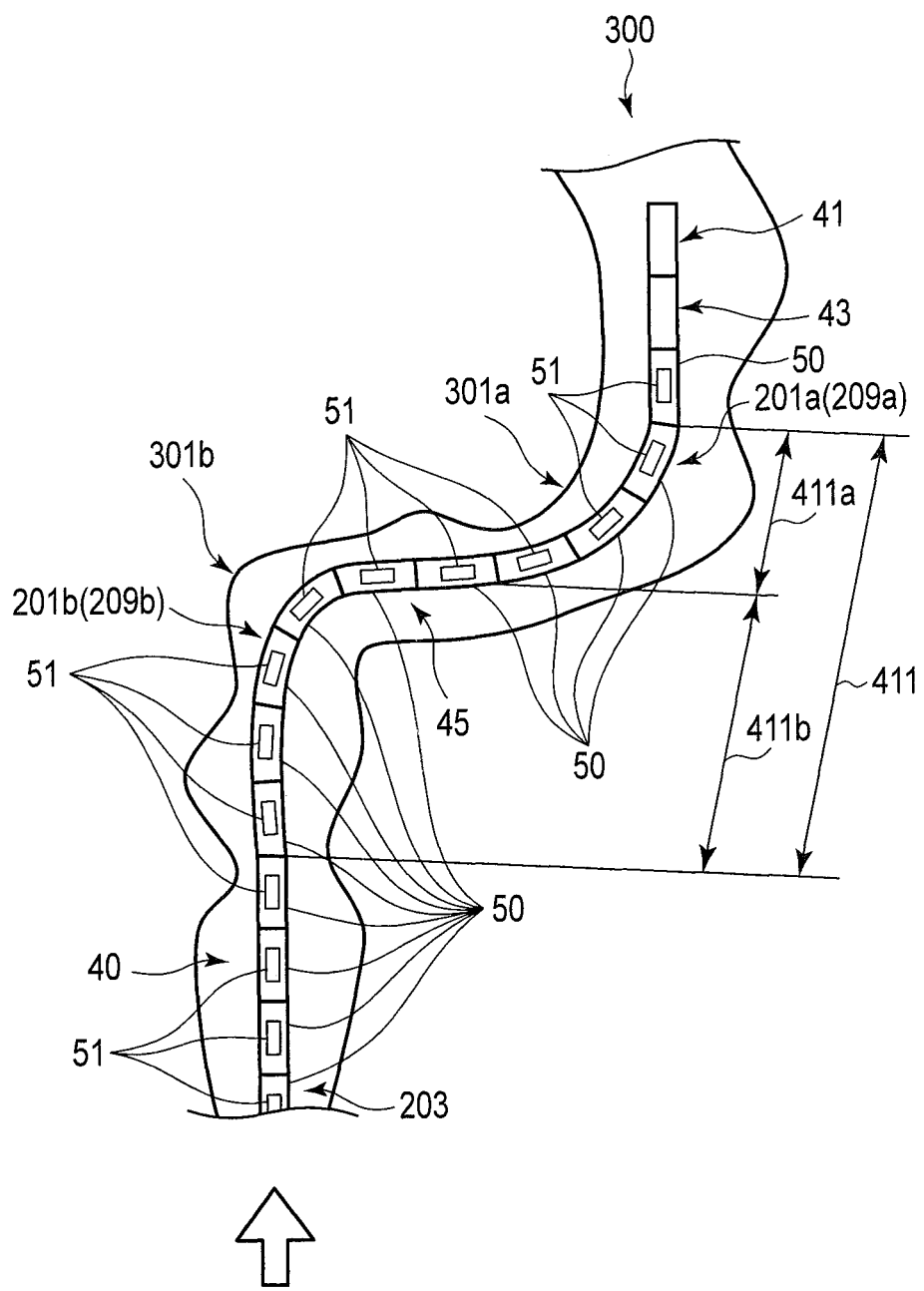
FIG. 10A is a diagram showing the stiffness variable portion provided in a segment arranged in a stiffness range decided by the stiffness change range decision portion.
Figure 11:
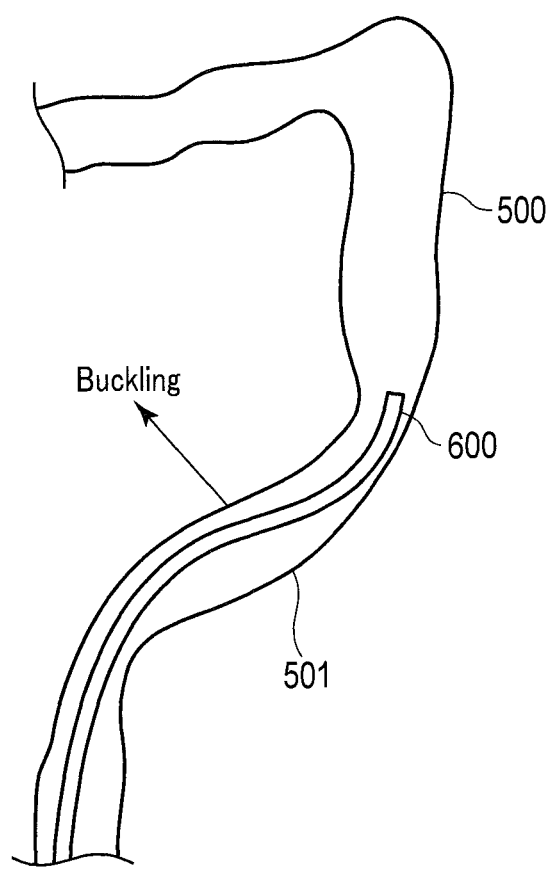
FIG. 11 is a diagram illustrating the insertion section buckling in an S-shape.

The control portion 129 controls the bending stiffness of the insertion section 40 in the stiffness change range 411 decided by the first decision portion 127, so as to be a bending stiffness that makes the insertion section 40 in the stiffness change range 411 substantially straight. As shown in FIGS. 10A and 10B, the control portion 129 controls the stiffness of the stiffness variable portions 51 corresponding to the segments 50 arranged in the stiffness change ranges 411a and 411b, in order to control the bending stiffness of the insertion section 40 to be the bending stiffness that makes the insertion section 40 substantially straight. The stiffness of the stiffness variable portions 51 that are shown in black in FIG. 10B is controlled.

The control portion 129 controls the stiffness of the stiffness variable portions 51 provided in the segments 50 arranged in the stiffness change range decided by the first decision portion 127, so that the state information of the insertion section 40 is adjusted to a target value set in advance.

An example of this control method will be described below.

As shown in FIG. 9A, the control portion 129 performs feedback control so that a deviation between a target value set in advance on the variable angle θ1 as the state information, and the variable angle θ1 as the state information of the insertion section 40 that is obtained from the detection unit 60 becomes zero. Thereby, the bent parts 201a and 201b become straight. The control portion 129 is, for example, a PID controller.

Another example of the control method will be described below.

For example, the control portion 129 may perform feedback control so that a deviation between a target value set in advance on the velocity ratio γ as the state information, and the velocity ratio γ as the state information of the insertion section 40 that is obtained from the detection unit 60 becomes zero, as shown in FIG. 9B. The control portion 129 is, for example, a PID controller.

Another example of the control method will be described below.

Figure 9D:
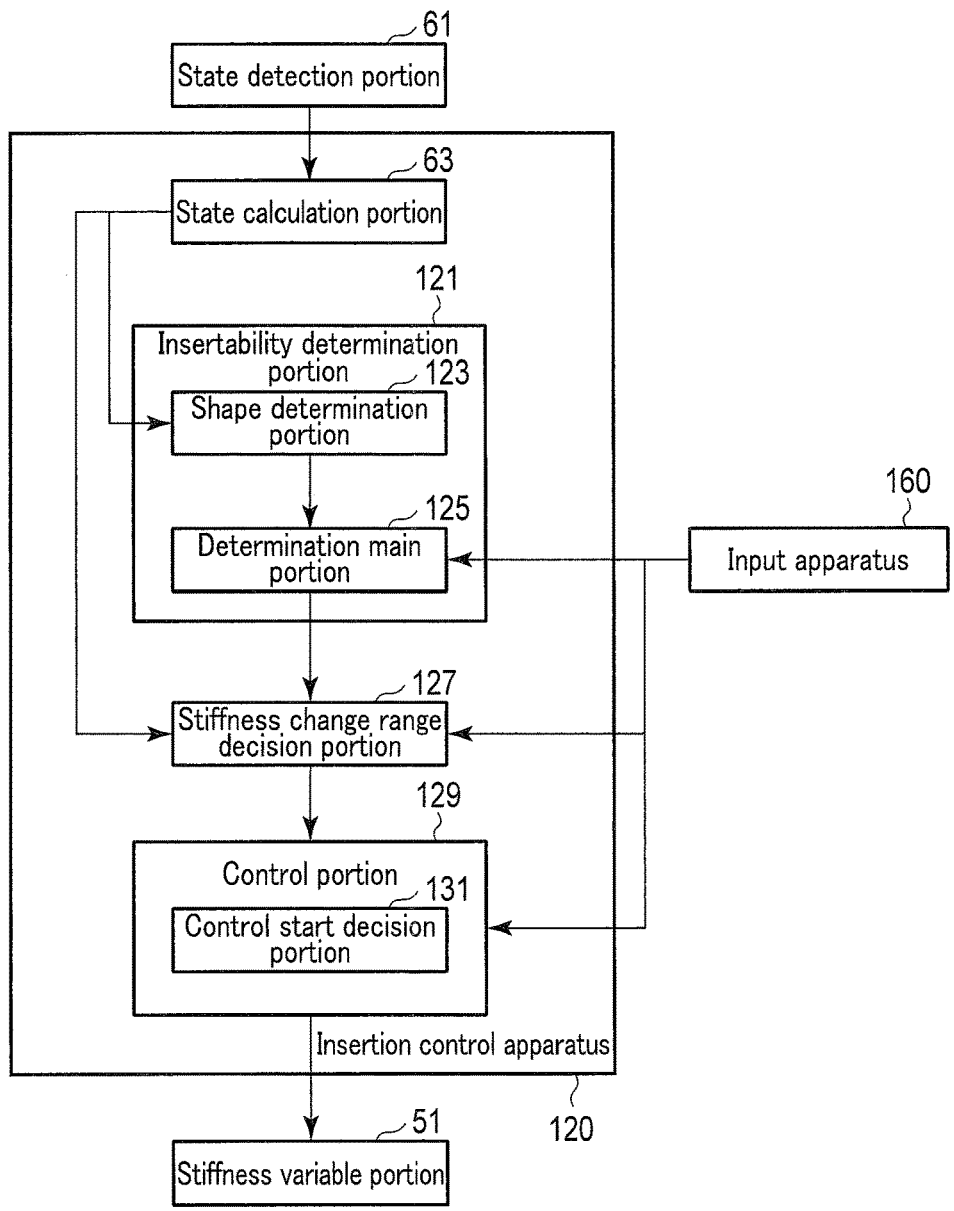
FIG. 9D is a diagram illustrating a relationship among the state detection portion, the state calculation portion, the insertability determination portion, the stiffness change range decision portion, the stiffness control portion, the stiffness variable portion, and the input apparatus, for the open control shown in FIG. 9C.

The control portion 129 may perform open control. As shown in FIGS. 9C and 9D, the control portion 129 inputs a stiffness variable signal (e.g., voltage signal) to the stiffness variable portions 51 in the stiffness change range 411 decided by the first decision portion 127. Then, the control portion 129 controls the stiffness variable portions 51 so that the stiffness of the stiffness variable portions 51 increases.

Next, an example of the decision (timing) of starting the control of the control portion 129 will be described.

Figure 9E:
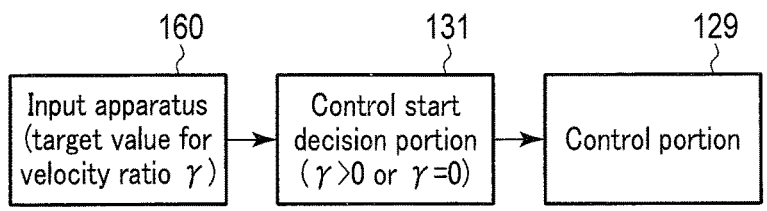
FIG. 9E is a diagram showing that a control start decision portion controls control timing for the stiffness variable portion based on a velocity ratio.

The control portion 129 may include a control start decision portion (hereinafter referred to as a second decision portion 131) that controls the control timing for the stiffness variable portions 51 based on the velocity ratio γ, as shown in FIGS. 2 and 9E. The velocity ratio γ is a ratio between the distal velocity Vout and the proximal velocity Vin that are shown in FIG. 3. For example, the operator grips the proximal end portion of the insertion section 40 that is exposed from the tube portion 300 to the outside, and pushes the insertion section 40 forward from this gripped part. At this time, the hand side force of the operator that pushes the insertion section 40 forward is transmitted from the gripped part to the distal end portion of the insertion section 40. Under such circumstances, in the case of γ>0, the hand side force at the proximal end portion (gripped part) is input to the distal end portion of the insertion section 40, so that the distal end portion of the insertion section 40 is in an inserted state. In the case of γ=1, the ratio is: distal velocity Vout: proximal velocity Vin=1:1. In the case of γ=0, the hand side force at the proximal end portion (gripped part) is not input to the distal end portion of the insertion section 40, so that the distal end portion of the insertion section 40 is in a stopped state.

For example, in the case of γ>0, the second decision portion 131 starts the control of the stiffness variable portions 51 in a state where the insertion section 40 is inserted, namely, in a state where the propulsion force of the distal end portion of the insertion section 40 has not dropped completely. In the case of γ=0, the second decision portion 131 starts the control of the stiffness variable portions 51 in a state where the insertion of the insertion section 40 is stopped, namely, in a state where the propulsion force of the insertion section 40 is lost.

Thereafter, the above-described feedback control or open control is performed.

For example, the distal velocity Vout may be detected by a first detection portion (not illustrated in the drawings) incorporated into the distal end portion of the insertion section 40. For example, the first detection portion is incorporated into the bendable portion 43. For example, the proximal velocity Vin may be detected by a second detection portion (not illustrated in the drawings) arranged at the entrance 300a of the tube portion 300. The first detection portion and the second detection portion are, for example, known sensors, such as an acceleration sensor or a magnetic sensor. In this manner, a method of calculating the distal velocity Vout and the proximal velocity Vin is not particularly limited.

[Input Apparatus 160]

As shown in FIG. 2, the input apparatus 160 outputs, to the detection unit 60, detection operation start instructions (detection start instruction and calculation start instruction) to start the operation of the detection unit 60, and outputs, to the shape determination portion 123, a determination start instruction to start the operation of the shape determination portion 123 of the determination portion 121. The input apparatus 160 outputs, to the first decision portion 127, a decision start instruction to start the operation of the first decision portion 127, and outputs, to the control portion 129 a control start instruction to start the operation of the control portion 129. The input apparatus 160 may output the detection operation start instructions, the determination start instruction, the decision start instruction, and the control start instruction either simultaneously or individually. The input apparatus 160 is, for example, a general input device, and is, for example, a pointing device such as a keyboard and a mouse, a tag reader, a button switch, a slider, and a dial.

The input apparatus 160 inputs the first threshold value to the determination main portion 125, inputs the second threshold value to the first decision portion 127, inputs a desired proportion to the first decision portion 127, inputs a desired angle to the control portion 129, and inputs a target value for the variable angle θ1 and a target value for the velocity ratio γ to the control portion 129. The input apparatus 160 performs this input before the insertion is performed, namely, before control of the control portion 129 is performed. Parameters including the first threshold value, second threshold value, desired proportion, desired angle, and target value may be stored in advance in a storage portion not illustrated in the drawings. Each portion may read the parameters from the storage portion by the input apparatus 160 outputting each start instruction to each portion.

The first threshold value and the second threshold value may be provisionally decided from insertion of the insertion section 40 into a training model of the large intestine or the pig's intestine. The provisionally decided first threshold value and second threshold value are slightly modified by the input apparatus 160 when the insertion section 40 is actually inserted. The slight modification may be performed using a suitable value calculated based on data of multiple actual results of cases stored in advance in the storage portion not illustrated in the drawings. An actual first threshold value and second threshold value are calculated by the control portion 129 based on the slightly-modified first threshold value and second threshold value. The calculated first threshold value is input to the determination main portion 125, and the calculated second threshold value is input to the first decision portion 127.

[Operation]

After the insertion apparatus 10 starts to be driven, the insertion section 40 is inserted from the entrance 300a into the tube portion 300, to be further inserted toward a deep portion. When the operator operates the input apparatus 160 and the input apparatus 160 outputs the detection operation start instruction to the detection unit 60, the state detection portion 61 detects the state information of the insertion section 40 in real time. The detection result detected by the state detection portion 61 is output to the state calculation portion 63 in real time. The state calculation portion 63 calculates the state information of the insertion section 40 in real time, on the basis of the detection result of the state detection portion 61. The state calculation portion 63 further calculates, in real time, state information of the tube portion 300 into which the insertion section 40 has been inserted, on the basis of the detection result of the state detection portion 61. The state calculation portion 63 outputs a calculation result calculated by the state calculation portion 63 to the display apparatus not illustrated in the drawings, the shape determination portion 123, the determination main portion 125, the first decision portion 127, and the control portion 129.

In accordance with an operation of the bending operation portion 31 on the bendable portion 43 and the operator's push operation, pull operation, and twist operation on the insertion section 40, the insertion section 40 passes through the bent portions 301a and 301b, as shown in FIG. 3. The display apparatus not illustrated in the drawings displays, using the state detection portion 61 and the state calculation portion 63, the shape of the insertion section 40 that is bent in accordance with the shape of the tube portion 300 and the bent portions 301a and 301b, and the insertion section 40 that passes through the bent portions 301a and 301b while bending. In this manner, the display apparatus not illustrated in the drawings displays the current state of the insertion section 40 in the tube portion 300 in real time, on the basis of the calculation result calculated by the state calculation portion 63. The operator monitors the position of the insertion section 40 in the tube portion 300 on the basis of the state of the insertion section 40 displayed on the display apparatus.

For insertion of the insertion section 40 toward a deep portion under a situation where the insertion section 40 is passing through the bent portions 301a and 301b, the operator grips the proximal end portion of the insertion section 40 exposed to the outside from the tube portion 300, and pushes the insertion section 40 forward from the gripped part. At this time, the bent parts 201a and 201b passing through the bent portions 301a and 301b may prevent the hand side force that pushes the insertion section 40 forward from being easily transmitted to the distal end portion of the insertion section 40 from the gripped part. Thereby, buckling may occur in the bent parts 201a and 201b, reducing the insertability of the insertion section 40 into a deep portion. The operator operates the input apparatus 160 under the monitored situation. The input apparatus 160 outputs the determination start instruction to the shape determination portion 123, outputs the decision start instruction to the first decision portion 127, and outputs the control start instruction to the control portion 129.

As shown in FIGS. 4A and 4B, the shape determination portion 123 of the determination portion 121, for example, calculates the angle θ2, and determines, in real time, whether the shape of the insertion section 40 is an S-shape or not based on the angle θ2. Namely, the shape determination portion 123 determines whether the shape of the insertion section 40 is an S-shape, as shown in FIG. 4A, or a shape other than an S-shape (e.g., U-shape), as shown in FIG. 4B. Now, let us assume that the angle θ2 is angle θ2>90° and that the shape determination portion 123 determines that the shape of the insertion section 40 is an S-shape. The shape determination portion 123 outputs the determination result to the determination main portion 125.

Next, let us assume that the shape determination portion 123 determines that the shape of the insertion section 40 is an S-shape, as shown in FIGS. 7A, 7B, and 7C, that the variable angle θ1 is equal to or less than 40°, which is the first threshold value, and that the relationship dθ/dt>0 is satisfied. In this case, the determination main portion 125 determines, in real time, that the insertability of the insertion section 40 is decreased by buckling.

The determination main portion 125 determines the decrease of the insertability of the insertion section 40 due to buckling based on the variable angle θ1, the first threshold value, and a temporal change of the variable angle θ1 or a temporal change of the curvature radii Ra and Rb. The determination main portion 125 prevents an erroneous determination that the insertability of the insertion section 40 is decreased when the insertion section 40 in an S-shape is successfully inserted toward a deep portion, as shown in FIG. 7D. The determination main portion 125 outputs the determination result to the first decision portion 127.

The first decision portion 127 decides, in real time, the range from the inflection point I to the first distant intersection point 405a as the stiffness change range 411a in the bent part 201a, as shown in FIGS. 8A and 10A. The first decision portion 127 also decides, in real time, the range from the inflection point I to the second distant intersection point 407a as the stiffness change range 411b in the bent part 201b. The determination main portion 125 outputs the decision result to the control portion 129.

The control portion 129 controls, in real time, the stiffness of the stiffness variable portions 51 provided in the segments 50 arranged in the stiffness change ranges 411a and 411b. Thereby, the variable angle θ1 is adjusted to a target value, and the stiffness variable portions 51 increase the stiffness so as to be substantially straight. Alternatively, the stiffness variable portions 51 increase the stiffness so as to be substantially straight without being affected by the variable angle θ1.

If the angle θ2 shown in FIG. 4 has been calculated, the control portion 129 may control the stiffness of the stiffness variable portions 51 so that the angle 82 has a target value (e.g., 180 degree). In this case, the input apparatus 160 inputs the target value of the angle 82 to the control portion 129. The input apparatus 160 performs this input before the insertion is performed, namely, before control of the control portion 129 is performed.

Therefore, the bent parts 201a and 201b turn into substantially straight parts 203a and 203b, as shown in FIGS. 10A and 10B. In accordance with this change, the bent portions 301a and 301b also turn into substantially straight portions 303a and 303b. That is, the control portion 129 changes the bent parts 201a and 201b to substantially straight parts 203a and 203b by controlling the stiffness of the stiffness variable portions 51, and changes the bent portions 301a and 301b to substantially straight portions 303a and 303b based on the substantially straight parts 203a and 203b. The control portion 129 relieves the bent portions 301a and 301b. The hand side force is efficiently transmitted from the gripped part to the distal end portion of the insertion section 40, and the substantially straight parts 203a and 203b are easily inserted toward a deep portion in the substantially straight portions 303a and 303b. That is, the insertion section 40 is easily advanced forward, thus improving the insertability of the insertion section 40. Since the substantially straight parts 203a and 203b are stiff, the hand side force is efficiently transmitted to the distal end portion of the insertion section 40 from the gripped part. Therefore, occurrence of buckling is prevented, and the insertability of the insertion section 40 into a deep portion is improved.

The stiffness of the stiffness variable portions 51 does not increase, and the bent parts 201a and 201b attempt to pass through the bent portions 301a and 301b in a bent state. In this case, the bent parts 201a and 201b may prevent the hand side force from being easily transmitted to the distal end portion of the insertion section, causing occurrence of buckling in the bent parts 201a and 201b. Also, even when the passing parts are substantially straight parts, buckling may occur if the stiffness of the substantially straight parts is low. If the stiffness of the substantially straight parts is low, the bent portions 301a and 301b cannot be changed to substantially straight portions, the bent portions 301a and 301b remain in a bent state, and the substantially straight parts having a low stiffness may not endure the pressure of the bent portions 301a and 301b and may be bent.

However, in the present embodiment, the bent parts 201a and 201b reliably change to the substantially straight parts 203a and 203b, the bent portions 301a and 301b reliably change to the substantially straight portions 303a and 303b based on the substantially straight parts 203a and 203b, and the bending stiffness of the substantially straight parts 203a and 203b is increased by the change in stiffness of the stiffness variable portions 51. Accordingly, a bend of the substantially straight parts 203a and 203b is prevented, the hand side force is efficiently transmitted from the gripped part to the distal end portion of the insertion section 40, and the insertion section 40 is easily inserted toward a deep portion, thus improving the insertability of the insertion section 40. Furthermore, since the hand side force is efficiently transmitted from the gripped part to the distal end portion of the insertion section 40, occurrence of buckling is prevented, and the insertability of the insertion section 40 into a deep portion is improved.

When the tube portion 300 is the large intestine, for example, and the insertion section 40 is passing through the sigmoid colon, which is represented by the bent portions 301a and 301b, the passing parts 209a and 209a passing through the sigmoid colon in the insertion section 40 are the bent parts 201a and 201b. By the change in stiffness of the stiffness variable portions 51, the bent parts 201a and 201b change to the substantially straight parts 203a and 203b, and the sigmoid colon (bent portions 301a and 301b) change to the substantially straight portions 303a and 303b by the substantially straight parts 203a and 203b. The bending stiffness of the substantially straight parts 203a and 203b is increased by the change in stiffness of the stiffness variable portions 51. Therefore, a bend of the substantially straight parts 203a and 203b is prevented, the hand side force is efficiently transmitted from the gripped part to the distal end portion of the insertion section 40, and thereby occurrence of buckling is prevented. Thus, the insertion section 40 is easily inserted toward the transverse colon located in a deeper portion of the large intestine than the sigmoid colon, and thereby the insertability of the insertion section 40 is improved. When the insertion section 40 that has been inserted from the sigmoid colon passes through the transverse colon, the bent parts corresponding to the sigmoid colon and the transverse colon are respectively changed to substantially straight parts, and the sigmoid colon and the transverse colon are changed to substantially straight portions by the substantially straight parts. This facilitates insertion toward the ascending colon located in a deeper portion of the large intestine than the transverse colon, and improves the insertability of the insertion section 40.

Some parts of the large intestine are not fixed within the abdomen, and are easily moved inside the abdomen. In particular, the large intestine is moved by an insertion operation of the insertion section 40, and insertion into the bent large intestine is not easy. However, the insertion section 40 is easily inserted toward a deep portion, as described above. Thus, the insertability is improved even if the state of the large intestine changes in accordance with insertion of the insertion section 40.

When the substantially straight parts 203a and 203b have completed passing through the substantially straight portions 303a and 303b, for example, the control portion 129 determines the passage on the basis of the calculation result (shape information of the insertion section 40 and shape information of the tube portion 300) of the state calculation portion 63. The control portion 129 decreases the stiffness of the stiffness variable portions 51 that are provided in the segments 50 arranged in the passage completion part of the insertion section 40 having completed passing through the substantially straight portions 303a and 303b and have a stiffness that makes the stiffness variable portions 51 substantially straight, to a desired stiffness. For example, the control portion 129 resets the controlled stiffness of the stiffness variable portions 51 to the initial stiffness at a desired timing. Thereby, the passage completion part is relieved from the substantially straight state, returns to the low strength part, and becomes bendable upon receiving an external force. Accordingly, the insertion section 40 can be bent along the shape of the tube portion 300. Let us assume that the operator monitors the position and the state of the insertion section 40 in the tube portion 300 via the display apparatus not shown in the drawings. Under such a situation, the operator may operate the input apparatus 160, and stop outputting various start instructions from the input apparatus 160. Thereby, the passage completion part is relieved from the substantially straight state, returns to the low strength part, and becomes bendable upon receiving an external force.

[Advantages]

In the present embodiment, the determination portion 121 determines whether the insertability of the insertion section 40 is decreased or not. If the insertability is decreased, the first decision portion 127 decides the stiffness change range 411 in a part of the insertion section 40 used for the determination of the determination portion. The control portion 129 controls the bending stiffness of the insertion section 40 in the stiffness change range 411 decided by the first decision portion 127.

Accordingly, in the present embodiment, the bent parts 201a and 201b can be changed to the substantially straight parts 203a and 203b, and the hand side force can be efficiently transmitted from the gripped part to the distal end portion of the insertion section 40, thus improving the insertability of the insertion section 40 into a deep portion. In the present embodiment, since the substantially straight parts 203a and 203b are stiff, and the hand side force can be efficiently transmitted to the distal end portion of the insertion section 40 from the gripped part, it is possible to prevent occurrence of buckling and to improve the insertability of the insertion section 40 into a deep portion. In the present embodiment, it is possible to improve the insertability into a deep portion, even if the state of the tube portion 300 changes in accordance with the insertion of the insertion section 40 into a deep portion. In the present embodiment, since occurrence of buckling can be prevented, it is possible to insert the insertion section 40 into a patient in a less-invasive manner. In the present embodiment, since the insertability of the insertion section 40 can be improved, it is possible to reduce the burden on the operator who operates the insertion apparatus 10.

In the present embodiment, in the determination portion 121, the shape determination portion 123 determines the shape of the insertion section 40 based on the state information of the insertion section 40, and the determination main portion 125 determines the decrease of the insertability of the insertion section 40 due to buckling based on the state information of the insertion section 40 and the determination result of the shape determination portion 123. Accordingly, in the present embodiment, the decrease of the insertability of the insertion section 40 can be determined with a simple configuration.

In the present embodiment, the shape determination portion 123 determines whether the shape of the insertion section 40 is an S-shape or not based on the angle θ2. Alternatively, the shape determination portion 123 determines whether the shape of the insertion section 40 is an S-shape or not based on the signs defined for the curvature radii Ra and Rb. Alternatively, the shape determination portion 123 determines whether the shape of the insertion section 40 is an S-shape or not based on the positions of the respective curvature centers Ca and Cb with respect to the tangential line 401a of the inflection point I. Accordingly, in the present embodiment, it is possible to determine whether the shape of the insertion section 40 is an S-shape or a shape other than an S-shape (e.g., U-shape), provide a determination material for the determination main portion 125, and surely improve the insertability of the insertion section 40.

In the present embodiment, the determination main portion 125 determines that the insertability of the insertion section 40 is decreased by buckling when the shape determination portion 123 determines that the shape of the insertion section 40 is an S-shape, and when the variable angle θ1 is equal to or less than the first threshold value, and the temporal change of the variable angle θ1 is positive or the temporal change of the curvature radii Ra and Rb is negative. Accordingly, in the present embodiment, the decrease of the insertability of the insertion section 40 due to buckling can be determined. Also, in the present embodiment, it is not simply determined that the insertability of the insertion section 40 is decreased when the shape of the insertion section 40 is an S-shape. Accordingly, in the present embodiment, it is possible to prevent an erroneous determination that the insertability of the insertion section 40 is decreased when the insertion section 40 in an S-shape is successfully inserted toward a deep portion.

In the present embodiment, the first decision portion 127 decides the stiffness change range 411 in the bent parts 201a and 201b, which are parts of the insertion section 40 used for the determination of the determination portion 121. Accordingly, in the present embodiment, the stiffness change range 411 can be suitably adjusted according to the situation of the tube portion 300, etc.

While the radius of curvature is used in the present embodiment, a curvature may be used instead. A curvature is a reciprocal of a radius of curvature. In this case, the second threshold value is a threshold value for a curvature.

In the present embodiment, the first decision portion 127 decides the range from the inflection point I to the first distant intersection point 405a as the stiffness change range 411a based on the second threshold value and the bend curve 403a. The first decision portion 127 decides the range from the inflection point I to the second distant intersection point 407a as the stiffness change range 411b based on the second threshold value and the bend curve 403b. In this manner, not all of the bent parts 201a and 201b are decided by the stiffness change range 411, and therefore the stiffness change range 411 can be suitably adjusted according to the situation of the tube portion 300, etc.

In the present embodiment, the first decision portion 127 decides a desired proportion of the range from the inflection point I to the first distant intersection point 405a as the stiffness change range 411a in the bent part 201a on the basis of the inflection point I, and decides a desired proportion of the range from the inflection point I to the second distant intersection point 407a as the stiffness change range 411b in the bent part 201b on the basis of the inflection point I. Accordingly, in the present embodiment, the stiffness change range 411 can be suitably adjusted according to the situation of the tube portion 300, etc. Also, in the present embodiment, since the bending stiffness can be changed around the inflection point I, the substantially straight parts 203a and 203b can be made to be continuous with each other, and the insertability of the insertion section 40 can be improved. In the present embodiment, the control portion 129 controls the stiffness of the stiffness variable portions 51 provided in the segments 50 arranged in the stiffness change range 411 decided by the first decision portion 127. Accordingly, the bending stiffness of the insertion section 40 can be controlled elaborately.

In the present embodiment, the control portion 129 controls the stiffness of the stiffness variable portions 51, and thereby it is possible to change the bent parts 201a and 201b into the substantially straight parts 203a and 203b, and to improve the insertibility of the insertion section 40.

In the present embodiment, the second decision portion 131 controls the control timing for the stiffness variable portions 51 based on the calculated velocity ratio γ. Accordingly, the control of the stiffness variable portions 51 can be started according to the insertion state or stopped state of the insertion section 40, and the insertability of the insertion section 40 can be improved. For example, in the case of γ>0, the stiffness variable portions 51 are controlled no matter how low the distal velocity Vout is. Therefore, it is possible to reliably change the bent parts 201a and 201b into the substantially straight parts 203a and 203b, and to improve the insertability of the insertion section 40. In the case of γ=0, the insertion of the insertion section 40 is in a stopped state. Namely, after the distal end of the insertion section 40 is once stopped, the stiffness variable portions 51 are controlled. By making the control timing adjustable in this manner, the timing of improving the insertability can be set according to the operator's preference. In addition, the second decision portion 131 may control the stiffness of the stiffness variable portions 51 so that the velocity ratio γ has a pre-set target value. Accordingly, it is possible to inhibit a decrease of the distal velocity Vout and the proximal velocity Vin, and to improve the insertability of the insertion section 40.

The determination portion 121 may determine whether the insertability of the insertion section 40 is decreased or not based on pattern matching. The shape determination portion 123 stores, in advance, the shape information of the insertion section 40 in which buckling occurs. The determination main portion 125 determines whether or not the current shape information of the insertion section 40 matches the shape information of the insertion section 40 stored in the shape determination portion 123. If the determination main portion 125 determines that the current shape information of the insertion section 40 matches the shape information of the insertion section 40 stored in the shape determination portion 123, the determination main portion 125 determines that the insertability of the insertion section 40 is decreased due to buckling. The storage portion not illustrated in the drawings may store, in advance, the shape information of the insertion section 40 in which buckling occurs, instead of the shape determination portion 123. The determination main portion 125 may read the shape information of the insertion section 40 stored in the storage portion.

For example, a training model of the large intestine or the pig's intestine is used in the shape information of the insertion section 40 stored in advance in the determination main portion 125. In this case, the insertion section 40 is inserted in advance into a deep portion of the training model or a deep portion of the pig's intestine. The determination main portion 125 stores the shape of the insertion section 40 at this time as the shape information of the insertion section 40 to be stored in advance. When the insertion section 40 is actually inserted, the determination main portion 125 slightly modifies the shape information of the insertion section 40 stored. The degree of the slight modification follows the operator's preference, for example. The slight modification is performed, for example, based on the state of the large intestine at the operator's judgment. The state of the large intestine represents stiffness, for example, and is determined based on the operator's experience.

The present invention is not limited to the above-described embodiment and can be embodied in practice by modifying the structural elements without departing from the gist of the invention. In addition, various inventions can be made by suitably combining the structural elements disclosed in connection with the above embodiment.

Additional advantages and variants will readily occur to those skilled in the art. Therefore, the invention in its broader aspects is not limited to the specific details and representative embodiments shown and described herein. Accordingly, various variants may be made without departing from the spirit or scope of the general inventive concept as defined by the appended claims and their equivalents.

What is claimed is:

1. A flexible tube insertion apparatus, comprising:
an insertion section that comprises a distal end and a proximal end and is inserted into a subject from the distal end;
a plurality of stiffness variable portions that are provided along a longitudinal direction of the insertion section, and are capable of changing a bending stiffness of the insertion section in a position where the plurality of stiffness variable portions are provided;
a detector that detects shape information indicating a shape of the insertion section;
at least one circuit that determines, based on the shape information, whether an S-shape that includes a first bent part forming an arc shape and a second bent part forming an arc shape and located distally on the first bent part with an inflection point between the first bent part and the second bent part is formed in the insertion section, determines whether an intersection angle between an extension line of a central axis of the insertion section located proximally on the first bent part and a tangential line for the insertion section at the inflection point is enlarged or not based on the shape information, and determines whether or not the stiffness variable portions are provided in a position of the S-shape in the insertion section when it is determined that the S-shape is formed in the insertion section and the intersection angle is enlarged; and
a stiffness controller that performs control that increases a stiffness of the stiffness variable portions included in the position of the S-shape in the insertion section, if it is determined that the stiffness variable portions are provided in the position of the S-shape in the insertion section.

2. The flexible tube insertion apparatus according to claim 1, wherein:
the shape information of the insertion section includes first and second curvature centers of first and second bent parts, respectively, that are continuous with each other in the insertion section, and the inflection point that is a connection part between the first and second bent parts; and
the at least one circuit determines whether the shape of the insertion section is an S-shape or not, based on an angle formed by a line segment that connects the first curvature center, the inflection point, and the second curvature center in the mentioned order.

3. The flexible tube insertion apparatus according to claim 1, wherein:
the shape information of the insertion section includes first and second curvature radii of first and second bent parts, respectively, that are continuous with each other in the insertion section, and the inflection point that is a connection part between the first and second bent parts; and
when a sign of a curvature radius of a bent part that is located on one side of the insertion section including the inflection point in an insertion direction of the insertion section is defined as "+", and a sign of a curvature radius of a bent part that is located on another side of the insertion section including the inflection point in the insertion direction is defined as "−", the at least one circuit determines whether the shape of the insertion section is an S-shape or not based on the signs defined for the respective first and second curvature radii.

4. The flexible tube insertion apparatus according to claim 1, wherein:
the shape information of the insertion section includes first and second curvature centers of the first and second bent parts, respectively, that are continuous with each other in the insertion section, and the inflection point that is a connection part between the first and second bent parts; and
the at least one circuit determines whether the shape of the insertion section is an S-shape or not based on positions of the respective first and second curvature centers with respect to the tangential line.

5. The flexible tube insertion apparatus according to claim 1, wherein:
the shape information of the insertion section includes: the intersection angle; and first and second curvature radii of the first and second bent parts, respectively; and
the at least one circuit determines that the insertability of the insertion section is decreased due to buckling, when it is determined that the shape of the insertion section is an S-shape, and when the intersection angle is equal to or less than a first threshold value, and a temporal change of the intersection angle is positive or a temporal change of a hand side curvature radius is negative.

6. The flexible tube insertion apparatus according to claim 1, wherein:
when it is determined that the intersection angle is enlarged, the at least one circuit decides a stiffness change range in a part of the insertion section used for the determination,
the stiffness controller controls the stiffness variable portions so that the bending stiffness of the insertion section in the stiffness change range is increased.

7. The flexible tube insertion apparatus according to claim 6, wherein:
the shape information of the insertion section includes: the first and second bent parts that are continuous with each other in the insertion section; the inflection point that is a connection part between the first and second bent parts; and a bend curve representing a relationship between the first and second bent parts and first and second curvature radii of the first and second bent parts, respectively;
based on a second threshold value, which is a value greater than the first and second curvature radii, and the bend curve, the at least one circuit calculates a first distant intersection point and a first close intersection point, which are intersection points between the second threshold value and the bend curve, in the first bent part;

the first distant intersection point is an intersection point that is away from the inflection point, and the first close intersection point is an intersection point that is close to the inflection point;

based on the second threshold value and the bend curve, the at least one circuit calculates a second distant intersection point and a second close intersection point, which are intersection points between the second threshold value and the bend curve, in the second bent part;

the second distant intersection point is an intersection point that is away from the inflection point, and the second close intersection point is an intersection point that is close to the inflection point; and the at least one circuit decides a range from the inflection point to the first distant intersection point as the stiffness change range in the first bent part, and decides a range from the inflection point to the second distant intersection point as the stiffness change range in the second bent part.

8. The flexible tube insertion apparatus according to claim 7, wherein the at least one circuit decides a desired proportion of the range from the inflection point to the first distant intersection point as the stiffness change range in the first bent part based on the inflection point, and decides a desired proportion of the range from the inflection point to the second distant intersection point as the stiffness change range in the second bent part based on the inflection point.

9. The flexible tube insertion apparatus according to claim 6, wherein:

the insertion section is divided into a plurality of segments arranged in a column shape along a longitudinal axis direction;

the stiffness variable portions change the bending stiffness of the insertion section in units of the segments; and the stiffness controller controls the stiffness of the stiffness variable portion corresponding to the segment arranged in the stiffness change range decided by the at least one circuit.

10. The flexible tube insertion apparatus according to claim 9, wherein:

the shape information of the insertion section includes: the inflection point that is a connection part between the first and second bent parts that are continuous with each other in the insertion section; and the intersection angle; and the stiffness controller controls the stiffness of the stiffness variable portion corresponding to the segment arranged in the stiffness change range decided by the at least one circuit, so that the intersection angle is adjusted to a preset target value for the intersection angle.

11. The flexible tube insertion apparatus according to claim 9, wherein:

the shape information of the insertion section includes a velocity ratio between a distal velocity at a distal end portion of the insertion section and a proximal velocity at a proximal end portion of the insertion section; and the stiffness controller controls the stiffness of the stiffness variable portion corresponding to the segment arranged in the stiffness change range decided by the at least one circuit, so that the velocity ratio is adjusted to a preset target value for the velocity ratio.

12. The flexible tube insertion apparatus according to claim 9, wherein:

the shape information of the insertion section includes a velocity ratio between a distal velocity at a distal end portion of the insertion section and a proximal velocity at a proximal end portion of the insertion section; and the stiffness controller determines a control timing for the stiffness variable portion based on the velocity ratio.

13. The flexible tube insertion apparatus according to claim 12, wherein the stiffness controller controls the stiffness of the stiffness variable portion so that the velocity ratio has a preset target value.

* * * * *